US009139601B2

(12) United States Patent
Buso et al.

(10) Patent No.: US 9,139,601 B2
(45) Date of Patent: Sep. 22, 2015

(54) CRYSTALLISATION FACILITATORS FOR THE SYNTHESIS OF METAL ORGANIC FRAMEWORKS

(75) Inventors: Dario Buso, Lancenigo (IT); Paolo Falcaro, Padua (IT)

(73) Assignee: COMMONWEALTH SCIENTIFIC AND INDUSTRIAL RESEARCH ORGANISATION, Campbell (AU)

( * ) Notice: Subject to any disclaimer, the term of this patent is extended or adjusted under 35 U.S.C. 154(b) by 257 days.

(21) Appl. No.: 13/695,190

(22) PCT Filed: Aug. 19, 2010

(86) PCT No.: PCT/AU2010/001056
§ 371 (c)(1),
(2), (4) Date: Apr. 15, 2013

(87) PCT Pub. No.: WO2011/133999
PCT Pub. Date: Nov. 3, 2011

(65) Prior Publication Data
US 2013/0204025 A1    Aug. 8, 2013

(30) Foreign Application Priority Data

Apr. 30, 2010    (AU) ............................... 2010901848
Apr. 30, 2010    (AU) ............................... 2010901850

(51) Int. Cl.
| C07F 3/00 | (2006.01) |
| C01B 39/00 | (2006.01) |
| C07F 3/06 | (2006.01) |
| C07F 9/38 | (2006.01) |

(52) U.S. Cl.
CPC . *C07F 3/06* (2013.01); *C01B 39/00* (2013.01); *C07F 3/003* (2013.01); *C07F 9/3839* (2013.01)

(58) Field of Classification Search
CPC ........ C01B 39/00; C07F 3/003; C07F 9/3839
USPC ......................................... 556/130; 423/305
See application file for complete search history.

(56) References Cited

U.S. PATENT DOCUMENTS

| 7,172,813 B2 | 2/2007 | Burgener, II et al. |
| 7,288,294 B2 | 10/2007 | Khang |
| 7,335,259 B2 | 2/2008 | Hanrath et al. |
| 7,465,352 B2 | 12/2008 | Cao |
| 2008/0177098 A1 | 7/2008 | Bahnmuller et al. |

FOREIGN PATENT DOCUMENTS

WO    WO 02/088148 A1    11/2002

OTHER PUBLICATIONS

Chinese official action dated Jul. 10, 2014 by the Chinese Patent Office, in connection with Chinese Patent Application No. 2010 80 066308.6.
Kim, Sang Bok et al., "Incorporation of Fe3O4 Nanoparticles into Organometallic Coordination Polymers by Nanoparticle Surface Modification", Angew. Chem. Int. Ed., vol. 48, 2009, p. 2907-2910.
Li, Yanshuo et al., "Zeolitic imidazolate framework ZIF-7 based molecular sieve membrane for hydrogen separation", Journal of Membrane Science, vol. 354, 2010, p. 48-54.
Petit, Camille et al., "Enhanced Adsoprtion of Ammonia on Metal-Organic Framework/Graphite Oxide Composites: Analysis of Surface Interactions", Adv. Funct. Mater., vol. 20, 2010, p. 111-118.
Koh, Kyoungmoo et al., "MOF@MOF: microporous core-shell architectures", Chem. Commun., 2009, p. 6162-6164.
Chen, S. et al. (2007). Dissipative particle dynamics simulation of gold nanoparticles stabilization by PEO-PPO-PEO block copolymer micelles. *Colloid and Polymer Science*, 285(14), 1543-1552.
Thuéry, P. (2009). A nanosized uranyl camphorate cage and its use as a building unit in a metal-organic framework. *Crystal Growth & Design*, 9(11), 4592-4594.
Solís, D. et al. (2008). Textural, structural and electrical properties of $TiO_2$ nanoparticles using Brij 35 and P123 as surfactants. *Science and Technology of Advanced Materials*, 9(2), 1-6.
Hermes, S. et al. (2007). Selective growth and MOCVD loading of small single crystals of MOF-5 at alumina and silica surfaces modified with organic self-assembled monolayers. *Chemistry of Materials*, 19(9), 2168-2173.
McNamara, W. R. et al. (2008). Acetylacetonate anchors for robust functionalization of $TiO_2$ nanoparticles with Mn(II)-Terpyridine complexes. *Journal of American Chemical Society*, 130(43), 14329-14338.
Communication including extended European Search Report, dated Feb. 4, 2014 by the European Patent Office, in connection with European Patent Application No. 10 85 0420.0, Commonwealth Scientific and Industrial Research Organisation.
Chen, S. et al. (2007). Dissipative particle dynamics simulation of gold nanoparticles stabilization by PEO—PPO—PEO block copolymer micelles. *Colloid and Polymer Science*. 285(14), 1543-1552.
An, Y. et al. (2007). Preparation and self-assembly of carboxylic acid-functionalized silica. *Journal of Colloid and Interface Science*, 311(2), 507-513.
Schröder, F. et al. (2008). Ruthenium nanoparticles inside porous $[Zn_4O(bdc)_3]$ by hydrogenolysis of adsorbed [Ru(cod)(cot)]: A solid-state reference system for surfactant-stabilized ruthenium colloids. *Journal of American Chemical Society*, 130(19), 6119-6130.
Müller, M. et al. (2008). Loading of MOF-5 with Cu and ZnO nanoparticles by gas-phase infiltration with organometallic precursors: Properties of Cu/ZnO@MOF-5 as catalyst for methanol synthesis. *Chemistry of Materials*, 20(14), 4576-4587.

(Continued)

*Primary Examiner* — Porfirio Nazario Gonzalez
(74) *Attorney, Agent, or Firm* — John P. White; Cooper & Dunham LLP

(57) ABSTRACT

A crystallization facilitator for promoting crystal growth of a metal-organic framework, the crystallization facilitator comprising at least one of: a metal or ionic form of that metal, or a compound including a metal, which is selected from the group consisting of Group 1 through 16 metals of the IUPAC Periodic Table of the Elements including actinides, and lanthanides, and combinations thereof. A method of synthesizing a metal-organic framework using the crystallization facilitator is also described.

20 Claims, 13 Drawing Sheets

(56) References Cited

OTHER PUBLICATIONS

Park, Y. K. et al. (2010). Catalytic nickel nanoparticles embedded in a mesoporous metal-organic framework. *Chemical Communications*, 46(18), 3086-3088.

Thuéry, P. (2009). A nanosized uranyl camphorate cage and its use as a building unit in a metal- organic framework. *Crystal Growth & Design*, 9(11), 4592-4594.

Solis, D. et al. (2008). Textural, structural and electrical properties of $TiO_2$ nanoparticles using Brij 35 and P123 as surfactants. *Science and Technology of Advanced Materials*, 9(2), 1-6.

Hermes, S. at al. (2007). Selective growth and MOCVD loading of small single crystals of MOF-5 at alumina and silica surfaces modified with organic self-assembled monolayers. *Chemistry of Materials*, 19(9), 2168-2173.

McNamara, W. R. et al. (2008). Acetylacetonate anchors for robust functionalization of $TiO_2$ nanoparticles with Mn(II)-Terpyridine complexes. *Journal of American Chemical Society*, 130(43), 14329-14338.

International Search Report, mailed Oct. 25, 2010 in connection with PCT International Application No. PCT/AU2010/001056, filed Aug. 19, 2010.

Written Opinion of the International Searching Authority, mailed Oct. 25, 2010 in connection with PCT International Application No. PCT/AU2010/001056, filed Aug. 19, 2010.

CRYSTALLISATION FACILITATORS FOR THE SYNTHESIS OF METAL ORGANIC FRAMEWORKS

CROSS-REFERENCE TO RELATED APPLICATIONS

This application is a §371 national stage of PCT International Application No, PCT/AU2010/001056, filed Aug. 19, 2010, claiming priority of Australian Patent Applications Nos. 2010901850, filed Apr. 30, 2010, and 2010901848, filed Apr. 30, 2010, the contents of each of which are hereby incorporated by reference in their entirety.

FIELD OF THE INVENTION

The present invention relates to crystallisation facilitators for the synthesis of metal organic frameworks, a method of synthesising metal organic frameworks using these crystallisation facilitators and the metal organic framework formed therefrom.

BACKGROUND OF THE INVENTION

The following discussion of the background to the invention is intended to facilitate an understanding of the invention. However, it should be appreciated that the discussion is not an acknowledgement or admission that any of the material referred to was published, known or part of the common general knowledge as at the priority date of the application.

Metal Organic Frameworks (MOFs) (also known as coordination polymers) are an emerging class of hybrid crystal materials where metal ions or small inorganic nano-clusters are linked into one-, two- or three-dimensional networks by multi-functional organic linkers. They have many appealing features having surface areas of thousands of square meters per gram, extremely low density, interconnected cavities and very narrow porosity distributions. A variety of open micro- and mesoporous structures can be developed, leading to materials with extreme surface area. Moreover, the possibility to arbitrarily engineer the cavities' architecture and the pores' surface chemistry makes metal organic frameworks excellent candidates for a wide variety of applications, from gas storage/separation to catalysis, drug delivery, optoelectronics and sensing.

Metal Organic Frameworks are also an emerging class of adaptive materials because they respond to external stimuli (light, electrical field, presence of particular chemical species), promising new advanced practical applications.

There are a large number of studies of the chemical structure and properties of metal organic frameworks. However, the applicants have only found a small number of studies investigating metal organic framework crystallisation mechanism. These studies suggest that conventional synthesis methods are largely based on the homogeneous crystallisation promoting of secondary building units (SBUs), which in turn join together to form the final crystal structure. Crystal growth can also proceed by a two-dimensional surface crystallisation promoting "birth and spread" mechanism.

Fischer et al (2005) *Journal of American Chemical Society*, 127, 13744-13745 indicated that the growth of a particular metal organic framework (MOF-5) crystal could be directed on 2D surfaces functionalised with self-assembled carboxy-terminated monolayers (SAMs). In this approach, SBUs or larger MOF-5 nuclei bind to $Zn^{2+}$ cations coordinated on the carboxylated SAMs via a terephthalate bridge. However, Fischer's research only points the way towards the development of metal organic framework based solid state devices and thin films. Furthermore, for a large scale production purpose the protocol is time-expensive as it requires a remarkable preparation time of more than 100 hours. In addition, the amount of MOF-5 that forms is limited by the planar surface area on which the SAM is deposited.

It would therefore be desirable to provide an alternative metal organic framework synthesis method. Preferably, this method would achieve fast, versatile (independent of substrate properties) and spatially controlled metal organic framework crystallisation.

SUMMARY OF THE INVENTION

According to a first aspect of the present invention, there is provided a metal-organic framework crystallisation facilitator for promoting crystal growth of a metal-organic framework, the crystallisation facilitator comprising nanoparticles or microparticles of at least one of:
  a compound comprising at least one of Zn, P, Si, B, C, Au or Al or ionic forms thereof combined with at least one of O, S, N or OH or ionic forms thereof; or
  at least one metal, metal chalcogenide or ionic, elemental form thereof,
wherein the crystallisation facilitator is captured within the formed metal organic framework.

The present invention also provides in a second aspect a method of synthesising a metal-organic framework including the steps of:
  providing a growing medium including precursors for forming a metal-organic framework comprising a plurality of metal clusters, each metal cluster including one or more metal ions; and a plurality of charged multidentate linking ligands connecting adjacent metal clusters;
  introducing a crystallisation facilitator according to the first aspect of the present invention or reagents which form a crystallisation facilitator according to the first aspect of the present invention into the growing medium; and
  inducing crystallisation promoting growth of the metal-organic framework, wherein the crystallisation facilitator is captured within the formed metal organic framework.

The crystallisation facilitator of the present invention speed the metal organic framework production rate. This can provide metal organic framework production at a substantially lower cost. It is considered that this is a step towards the effective scale-up of metal organic framework production. It is to be understood that the term crystallisation facilitator includes crystallisation promoting agent, crystallisation nucleating agent, crystallisation growth stimulator and the like.

The particles of crystallisation facilitator are preferably particles, more preferably nanoparticles or microparticles. These micro and/or nano-sized seeds provide a large surface area to promote metal organic framework formation. It was found that a metal-organic framework is formed on and around each microparticle and/or nanoparticle of crystallisation facilitator. In a preferred form, the crystallisation facilitator comprises a plurality of substantially spherical shaped particles, nanoparticles and/or microparticles. In some forms, the crystallisation facilitator comprises microspheres.

The crystallisation facilitator can be added into a growth medium as a mixture of particles or alternatively provided in or on a substrate. Provision of the crystallisation facilitator on a substrate can enable spatially controlled metal organic framework crystallisation. The configuration of metal organic framework crystal structures can therefore be controlled through selective and designer placement of the crystallisation facilitator in or on the substrate. In one form, the substrate comprises a lithographed substrate seeded with particles of the crystallisation facilitating agent.

The crystallisation facilitator according to the present invention is preferably a metal or ionic form of that metal is selected from at least one of Li, Na, K, Rb, Be, Mg, Ca, Sr, Ba, Sc, Y, Ti, Zr, Hf, V, Nb, Ta, Cr, Mo, W, Mn, Re, Fe, Ru, Os, Co, Rh, Ir, Ni, Pd, Pt, Cu, Ag, Au, Zn, Cd, Hg, B, Al, Ga, In, Tl, Si, Ge, Sn, Pb, As, Sb, Bi, or combinations thereof.

In some embodiments, the crystallisation facilitator comprises a compound comprising at least one of Zn, P, Si, B, C, Au or Al or ionic forms thereof combined with at least one of O, S, N or OH or ionic forms thereof. In some forms, the crystallisation facilitator can comprise any suitable metal phosphate or functional equivalent. In one exemplary embodiment, the crystallisation facilitator comprises particles of zinc phosphate or functional equivalents. In one exemplary form, the crystallisation facilitator comprises poly-hydrate zinc phosphate nanoflaked desert-rose microparticles.

In some embodiments, the compound has a chemical functionality including at least one of vinyl-, mercapto-, carboxyl-, hydroxyl, or other alkyl-groups.

In other embodiments, the crystallisation facilitator comprises particles of at least one metal, metal chalcogenide or ionic, elemental form thereof. In these embodiments, the metal or the metal chalcogenide of the crystallisation facilitator may have at least one of amino-, carboxyl-, or hydroxyl-functionalised surfaces. In one exemplary embodiment, the crystallisation facilitator comprises particles of silicon dioxide with at least one of amino-, carboxyl-, or hydroxyl-functionalised surfaces.

The particles of metal chalcogenide used in certain embodiments of the present invention can be produced by any suitable method. One preferred method of producing metal chalcogenide for the present invention is a sol gel method.

In some embodiments, the crystallisation facilitators are nanoparticles or microparticles of metals or metal chalcogenides. In preferred embodiments, metal nanoparticles or microparticles can be made of element or ionic form thereof M selected from at least one of Li, Na, K, Rb, Be, Mg, Ca, Sr, Ba, Sc, Y, Ti, Zr, Hf, V, Nb, Ta, Cr, Mo, W, Mn, Re, Fe, Ru, Os, Co, Rh, Ir, Ni, Pd, Pt, Cu, Ag, Au, Zn, Cd, Hg, B, Al, Ga, In, Tl, Si, Ge, Sn, Pb, As, Sb, Bi, or their combinations.

The metal or ionic form of that metal is magnetic, and preferably at least one of ferromagnetic, paramagnetic, superparamagnetic.

Metal chalcogenides which can be used as crystallisation facilitators for the present invention can be compound including any combination of the previous elements or ionic form M in combination with elements or elemental form of at least one of O, S, Se, or Te. In some embodiments, the crystallisation facilitators comprise metal chalcogenide having the formula $M_xN_yC_z$, where M,N are selected from at least one of Li, Na, K, Rb, Be, Mg, Ca, Sr, Ba, Sc, Y, Ti, Zr, Hf, V, Nb, Ta, Cr, Mo, W, Mn, Re, Fe, Ru, Os, Co, Rh, Ir, Ni, Pd, Pt, Cu, Ag, Au, Zn, Cd, Hg, B, Al, Ga, In, Tl, Si, Ge, Sn, Pb, As, Sb, Bi, C is selected from at least one of O, S, Se, Te, x is any number from 0 to 10, y is any number from 0 to 10 and z is any number from 0 to 10. The metal chalcogenide nanoparticles may in some embodiments have a core-shell structure in which the core comprises at least one metal chalcogenide as previously described and the shell comprises at least one metal chalcogenide as previously described. In some forms, the core-shell structure may include multiple shells.

Certain crystallisation facilitators can provide luminescent properties to the MOF. Examples include CdSe, CdS and ZnS.

The crystallisation facilitator of the present invention can be produced by any suitable method.

When synthesising the metal organic frameworks, the nano- or micro particulate crystallisation facilitator can be formed within the growing medium from precursor compounds introduced into the growing medium or the growing medium may be inoculated with the nanoparticulate crystallisation facilitator. In the former, precursor material can be added into the growing medium which reacts within that medium to form the particles of crystallisation facilitator. In the latter, the particles of crystallisation facilitator are prefabricated, pre-synthesised and then inoculated into the growing medium.

In those embodiments where the crystallisation facilitator comprises a metal chalcogenide, and more particularly particles of metal phosphate, the metal chalcogenide can be produced from a precursor material added to the growth medium. The precursor material preferably includes a metal precursor and optionally an organic precursor. In one embodiment, the precursor material added to the growth medium includes a non-ionic triblock copolymer surfactant, preferably the family of PEO—PPO—PEO amphiphlilic molecules, for example Pluronic F-127. This precursor can be added to a growing medium to form the crystallisation facilitator in a one pot method of synthesis.

The use of crystallisation facilitators has also been found to enable the addition of functional species into the metal organic framework. In this respect, certain functional species can be encapsulated within the metal organic framework at or around the location of the crystallisation facilitator.

The synthesis method can therefore further comprise introducing a functional species into the growing medium, the functional species being encapsulated within or attached to the nanoparticles of the crystallisation facilitator within the metal organic framework. Suitable functional species including transition metal nanoparticles (Sc, Y, Hf, Cr, Mn, Ca, Li, Na, K, Cs, Fr, Be, Mg, Ca, Sr, Ba, Ra, Pt, Pd, Au, Ru, Rb, Ag, Ni, Co, Os, Ir, Ti, Fe, V, Zr, W, Hf, Ta, Hg), other metallic nanoparticles (Si, Gs, Ge, In, Sn, Sb, Tl, Pb, Bi, Po, Al, Ga), nanoparticles containing lanthanide or actinide elements (Ce, Pr, Nd, PM, Sm, Eu, Gd, Tb, Dy, Ho, Er, Tm, Yb, Lu, Th, Pa, U, Np Pu, Am, Cm, Bk, Cf, Es, Fm, Md, No, Lr) with nanoparticles prepared with non-metals (B, C, Si, P, As, Se) or ceramic nanoparticles based on one or a combination of the previously mentioned elements with elements (O, S, Se, Te) and other reactive and active compounds. The crystallisation facilitators can therefore allow for the controlled insertion of functional species inside the metal organic framework crystals.

In other embodiments, functional species the functional species being encapsulated within or attached to the nanoparticles of the crystallisation facilitator within the metal organic framework comprises at least one of a polymeric particle, microparticle or nanoparticle, a particle, microparticle or nanoparticle. Suitable polymeric particle include polymer or copolymer formed from at least one of the following monomers Ethylene, Propylene, Vinyl fluoride, Vinylidene fluoride, Tetrafluoroethylene, Hexafluoropropylene, Perfluoropropylvinylether, Perfluoromethylvinylether, Chlorotrifluoroethylene. One suitable example is Polytetrafluoroethylene.

In some forms, the crystals can be used as filters/sieves to select what can react/interact with the functional species within these crystals. The functional species inserted using the crystallisation facilitators as vehicles are typically completely encapsulated within the metal organic framework structure. This is better than impregnation techniques for metal organic frameworks where the functional species are detected also on the external surfaces of the crystals.

The crystallisation facilitators can be used to nucleate and/or grow a metal-organic framework, as set out in the second aspect of the present invention. The precursors for forming a metal-organic framework preferably comprise a plurality of metal clusters, and a plurality of charged multidentate linking ligands connecting adjacent metal clusters. Each metal cluster includes one or more metal ions As used herein, the term "cluster" means a moiety containing one or more atoms or ions of one or more metals or metalloids. This definition embraces single atoms or ions and groups of atoms or ions that optionally include ligands or covalently bonded groups.

Each cluster preferably comprises two or more metal or metalloid ions (hereinafter jointly referred to as "metal ions") and each ligand of the plurality of multidentate ligand includes two or more carboxylates.

Typically, the metal ion is selected from the group consisting of Group 1 through 16 metals of the IUPAC Periodic Table of the Elements including actinides, and lanthanides, and combinations thereof. Preferably, the metal ion is selected from the group consisting of $Li^+$, $Na^+$, $K^+$, $Rb^+$, $Be^{2+}$, $Mg^{2+}$, $Ca^{2+}$, $Sr^{2+}$, $Ba^{2+}$, $Sc^{3+}$, $Y^{3+}$, $Ti^{4+}$, $Zr^{4+}$, $Hf^{4+}$, $V^{4+}$, $V^{3+}$, $V^{2+}$, $Nb^{3+}$, $Ta^{3+}$, $Cr^{3+}$, $Mo^{3+}$, $W^{3+}$, $Mn^{3+}$, $Mn^{2+}$, $Re^{3+}$, $Re^{2+}$, $Fe^{3+}$, $Fe^{2+}$, $Ru^{3+}$, $Ru^{2+}$, $Os^{3+}$, $Os^{2+}$, $Co^{3+}$, $Co^{2+}$, $Rh^{2+}$, $Rh^+$, $Ir^{2+}$, $Ir^+$, $Ni^{2+}$, $Ni^+$, $Pd^{2+}$, $Pd^+$, $Pt^{2+}$, $Pt^+$, $Cu^{2+}$, $Cu^+$, $Ag^+$, $Au^+$, $Zn^{2+}$, $Cd^{2+}$, $Hg^{2+}$, $B^{3+}$, $B^{5+}$, $Al^{3+}$, $Ga^{3+}$, $In^{3+}$, $Tl^{3+}$, $Si^{4+}$, $Si^{2+}$, $Ge^{4+}$, $Ge^{2+}$, $Sn^{4+}$, $Sn^{2+}$, $Pb^{4+}$, $Pb^{2+}$, $As^{5+}$, $As^{3+}$, $As^+$, $Sb^{5+}$, $Sb^{3+}$, $Sb^+$, $Bi^{5+}$, $Bi^{3+}$, $Bi^+$, and combinations thereof.

Typically, the cluster has formula $M_m X_n$ where M is metal ion, X is selected from the group consisting of Group 14 through Group 17 anion, m is an number from 1 to 10, and n is a number selected to charge balance the cluster so that the cluster has a predetermined electric charge Preferably, X is selected from the group consisting of $O^{2-}$, $N^{3-}$ and $S^{2-}$. Preferably, M is selected from the group consisting of $Li^+$, $K^+$, $Na^+$, $Cs^+$, $Mg^{2+}$, $Ca^{2+}$, $Sr^{2+}$, $Ba^{2+}$, $V^{2+}$, $V^{3+}$, $V^{4+}$, $V^{5+}$, $Mn^{2+}$, $Re^{2+}$, $Fe^{3+}$, $Fe^{2+}$, $Ru^{3+}$, $Ru^{2+}$, $Os^{2+}$, $Co^{2+}$, $Rh^{2+}$, $Ir^{2+}$, $Ni^{2+}$, $Pd^{2+}$, $Pt^{2+}$, $Cu^{2+}$, $Zn^{2+}$, $Cd^{2+}$, $Hg^{2+}$, $Si^{2+}$, $Ge^{2+}$, $Sn^{2+}$, and $Pb^{2+}$. More preferably M is $Zn^{2+}$ and X is $O^{2-}$.

Typically, the multidentate linking ligand has 6 or more atoms that are incorporated in aromatic rings or non-aromatic rings. Preferably, the multidentate linking ligand has 12 or more atoms that are incorporated in aromatic rings or non-aromatic rings. More preferably, the one or more multidentate linking ligands comprise a ligand selected from the group consisting of ligands having formulae 1 through 27:

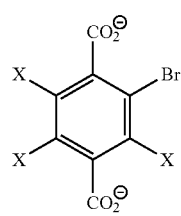

1

-continued

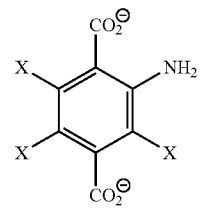

2

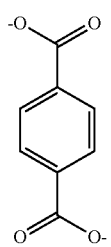

3

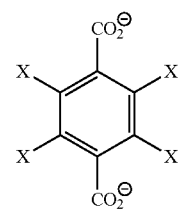

4

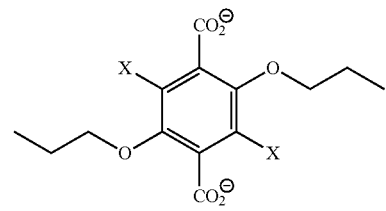

5

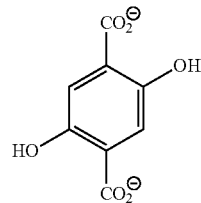

6

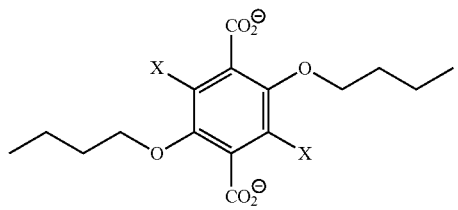

7

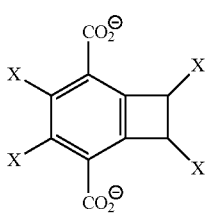

8

9
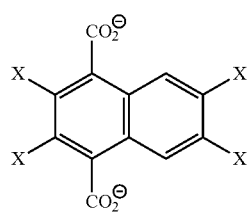
10
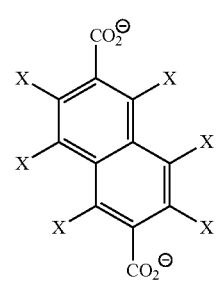
11
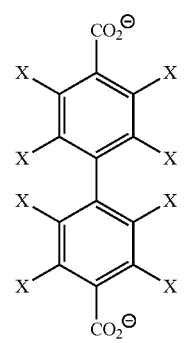
12
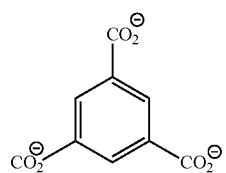
13
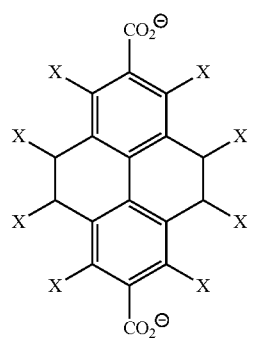
14
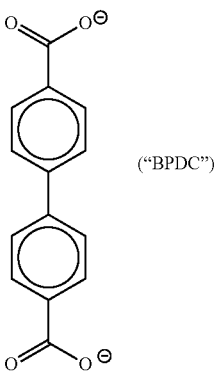
("BPDC")
15
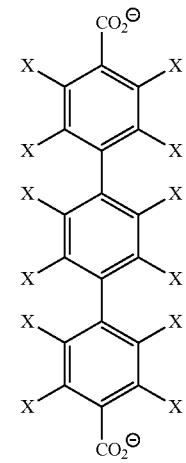
16
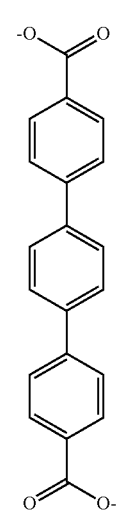
17
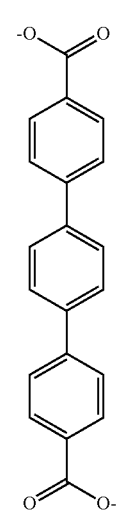

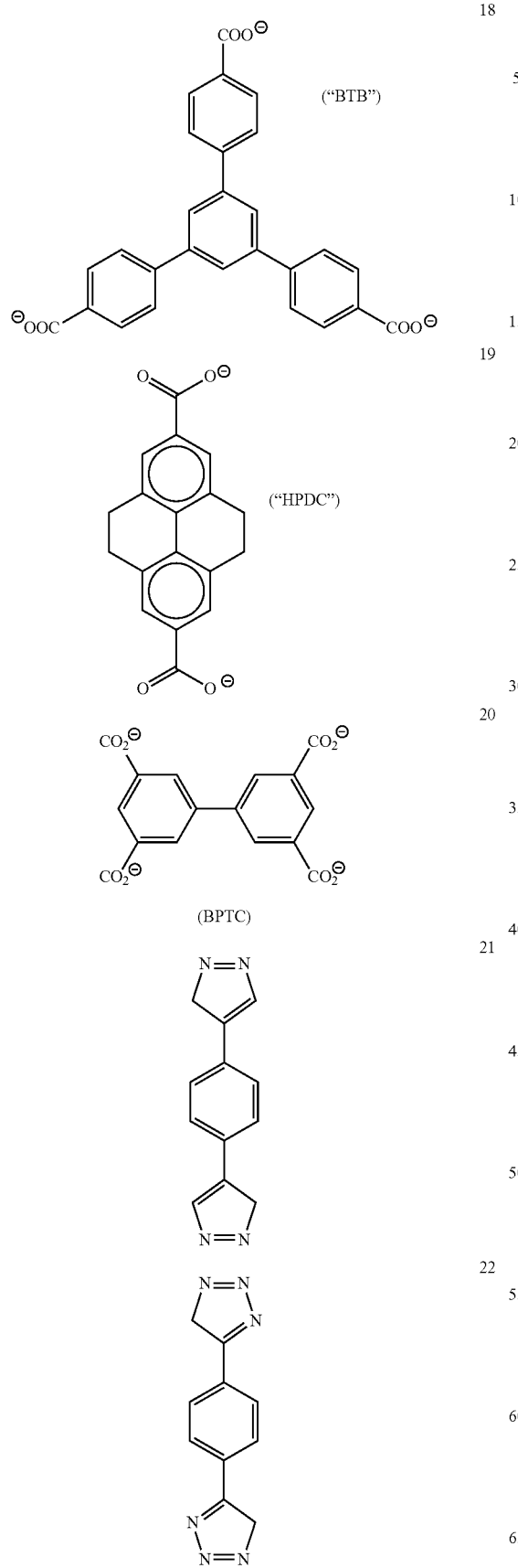
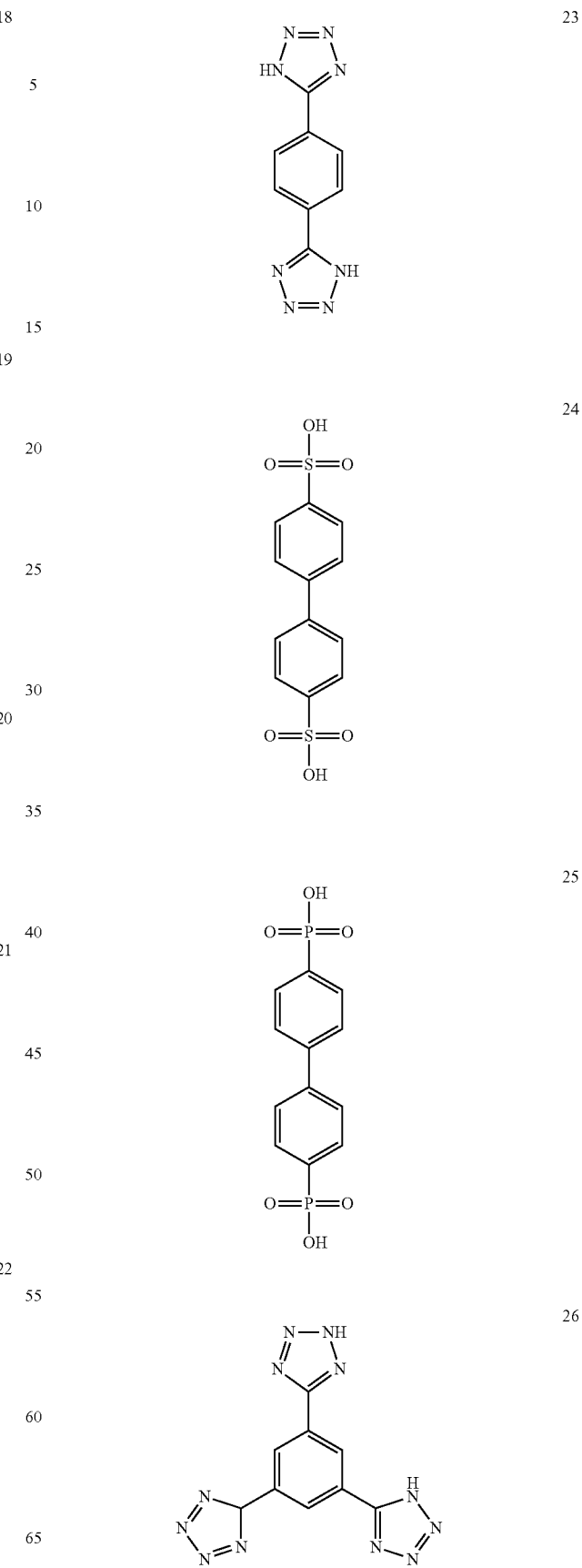

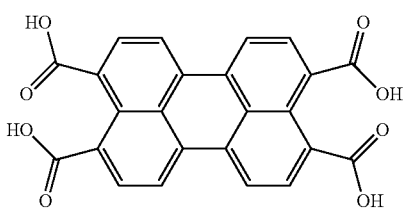

27 wherein X is hydrogen, —NHR, —N(R)$_2$, halides, C$_{1-10}$ alkyl, C$_{6-18}$ aryl, or C$_{6-18}$ aralkyl, —NH$_2$, alkenyl, alkynyl, —Oalkyl, —NH(aryl), cycloalkyl, cycloalkenyl, cycloalkynyl, —(CO)R, —(SO$_2$)R, —(CO$_2$)R —SH, —S(alkyl), —SO$_3$H, —SO$^{3-}$M$^+$, -COOH, —COO$^-$M$^+$, —PO$_3$H$_2$—, —PO$_3$H$^-$M$^+$, —PO$_3{}^{2-}$M$^{2+}$, or —PO$_3{}^{2-}$M$^{2+}$, —NO$_2$, —CO$_2$H, silyl derivatives; borane derivatives; and ferrocenes and other metallocenes; M is a metal atom, and R is C$_{1-10}$ alkyl.

In one embodiment, the multidentate linking ligand comprises a ligand having formula 3 previously described. In another embodiment, the multidentate linking ligand comprises a ligand having formula 18 ("BTB"). In a further embodiment, the multidentate linking ligand comprises a ligand having formula 14. Examples of metal organic frameworks which may be suitable for use in the present invention include those commonly known in the art as MOF-177, MOF-5, IRMOF-1 or IRMOF-8. In a preferred embodiment, the metal-organic framework is MOF-5.

The crystallisation facilitators can be used to nucleate and/or grow a metal-organic framework including a crystallisation facilitator according to the first aspect of the present invention, a plurality of metal clusters, each metal cluster including one or more metal ions; and a plurality of charged multidentate linking ligands connecting adjacent metal clusters.

The metal organic frameworks formed from the method of the present invention have a number of applications, including gas storage and release, gas separation and gas cleaning. Here, the spatial control of metal-organic framework formation allows for the production of continuous membranes of metal-organic frameworks or alternatively, the control of the metal-organic framework growth in confined areas. The metal organic framework formed from the method of the present invention may also be used in catalysis for the production of selective catalysts; pharmaceutical applications for the production of crystal units for the controlled release of drugs; in the automotive industry where the fast reaction rates are advantageous for the production of metal-organic frameworks for gas storage units in large scale; and in sensors where the use of functional species implanted in the metal-organic framework may allow for better selectivity for molecular detection.

In order that the invention can be more readily understood, non-limiting embodiments thereof are now described with reference to the accompanying drawings.

BRIEF DESCRIPTION OF THE DRAWINGS

The invention will now be described in greater detail with reference to embodiments illustrated in the accompanying drawings.

DETAILED DESCRIPTION OF PREFERRED EMBODIMENTS

Example 1

Desert-Rose Microparticles

This aspect of the present invention provides a new synthesis method for the formation of inorganic nanoflake microparticles, here named desert-rose microparticles (DRMs), with the exceptional capability to nucleate the crystal growth of metal organic frameworks (MOFs) in a MOF crystal growth medium. These crystallisation facilitator particles provide crystallisation promoting sites for the metal organic framework within a crystal growth medium. The studied crystallisation facilitators are zinc-phosphate compounds, though it should be appreciated that other metal chalcogenide compounds may also be suitable.

The described method combines surfactants with solvothermal MOF-5 syntheses in a one-pot protocol. MOF-5 was used as an example of a metal organic framework that can be grown using the crystallisation facilitators of the present invention. MOF-5 is one of the most studied metal-organic frameworks and it was a benchmark material for proving numerous concepts and properties. It should be understood that MOF-5 was used for example purposes only, and that a large variety of other metal organic frameworks could be nucleated and grown using the below described techniques.

1.1 One-Pot Synthesis of DRMs Encapsulated in MOF-5

Experimental

N,N dimethylformamide (DMF), Zinc nitrate hexahydrate, Benzene-1,4-dicarboxylic acid Terephthalic acid, TA) and Pluronic F-127 were purchased from Sigma-Aldrich and used without further purification.

A colourless and transparent Zinc Nitrate (0.001 M to 6 M) and TA (0.0001 M to 8 M) solution in DMF was first prepared. In a typical synthesis, 3.5 mL aliquots of this mother solution were prepared, and a quantity between 0.01 to 10 g of Pluronic F-127 was added to each of the aliquots. The aliquots were transferred into Teflon sealed glass vials, and eventually heated in a MRC dry bath incubator (Thermoline Scientific) pre-set at temperatures in the range 75 to 130° C. The DRMs used for further experiments were extracted after 3 hours using fritted glass filters (n. 1), and then re-dispersed in fresh DMF.

Synthesis of MOF-5 in N,N Diethylformamide (DEF)

All the DEF-based MOF-5 growing media used in the experiments with DRMs were realised using the same procedure described above, using DEF instead of DMF.

Results

A rapid formation of a cloudy suspension is obtained by the addition of F-127 to the solution of MOF-5 precursors. Pluronic F-127 is also a source of phosphorous. Both the polymer and the phosphorous play a fundamental role in the fast isodirectional formation of the poly-hydrate zinc phosphate nanoflaked desert-rose microparticles (DRMs) in the MOF-5 growing medium. A characterization of these desert-rose microparticles is presented later in the specification. These DRMs provide a heterogeneous crystallisation facilitating surface in the growth medium.

Figure 1:
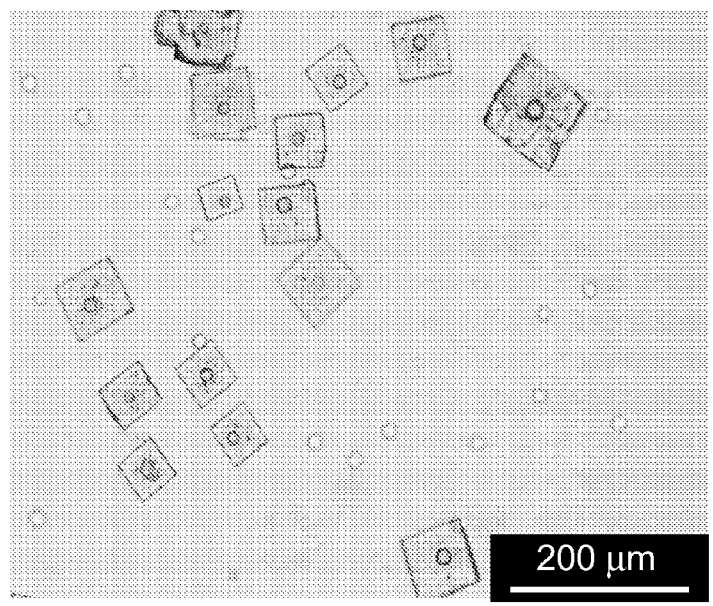
FIG. 1 provides optical microscope images of a metal organic framework crystal growth after 5 hours in a N,N dimethylformamide solution (DMF) with a crystallisation facilitator added according to one embodiment of the present invention.

In the experiments, the formation of DRMs was detected within few minutes of reaction. Depending on the concentration of surfactant, different densities of DRMs per unit volume are detected. After 5 hours reaction, MOF-5 starts to nucleate on the microparticles surface, as depicted in the optical microscope images of FIGS. 1 and 2.

Figure 2:
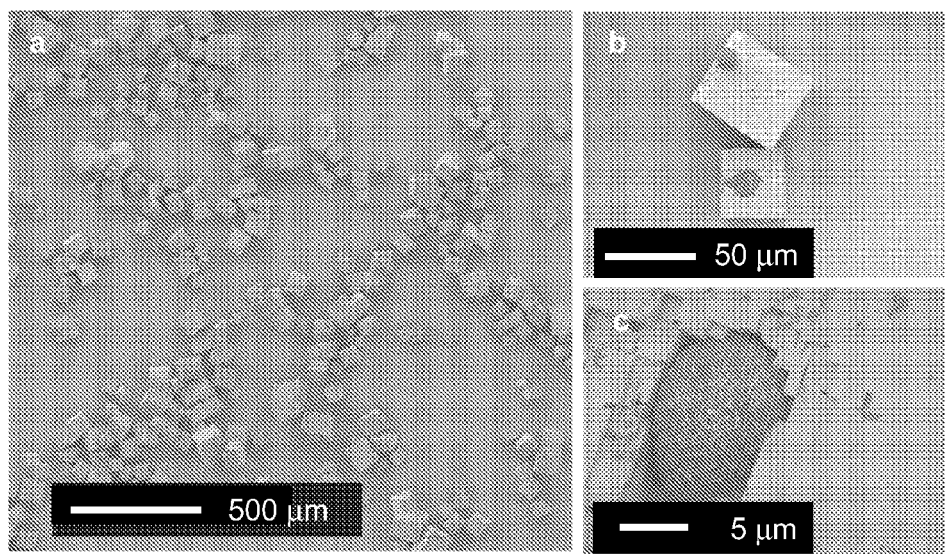
FIG. 2 provides SEM images of MOF-5 crystals synthesized using a one-pot synthesis method using a crystallisation facilitator added according to one embodiment of the present invention.

The optical microscope image of FIG. 1(a) shows the DRMs embedded in the surfactant suspension after 3 hours heating. In about 5 hours the MOF crystals start crystallisation promoting on DRMs (FIG. 2). After 8 hours the DRMs are completely encapsulated in the crystals. This surfactant-directed synthetic route reduces the MOF-5 processing three times faster when compared with conventional solvothermal methods.

Microscopy indicates that more than 90% of the crystals formed during the surfactant assisted synthesis using dimethyl formamide (DMF) contain the DRMs (as best shown in FIG. 1(b)).

Figure 3:
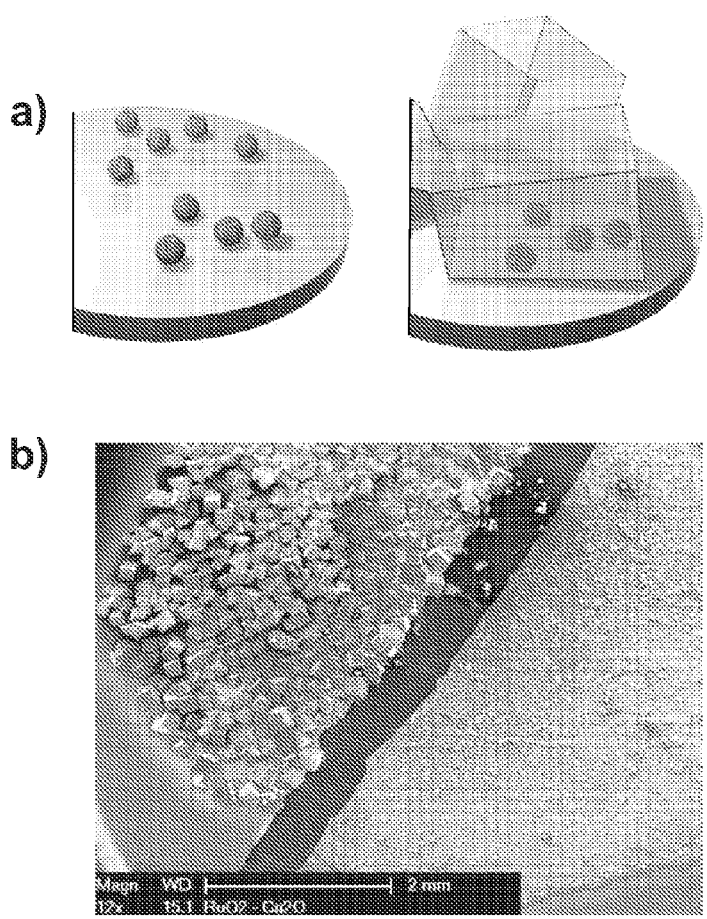
FIG. 3(a) provides a diagrammatic representation of the seeding and subsequent metal organic framework crystal growth on an alumina substrate seeded with a crystallisation facilitator added according to one embodiment of the present invention.
FIG. 3(b) provides optical microscope images and corresponding diagrammatic illustrations of MOF crystal deposited on the alumina substrate illustrated in FIG. 3(a).

In FIG. 3, SEM images of MOF-5 synthesized using the surfactant-directed method reveal that the spherical shape of the DRMs is produced by the arrangement of multiple 150 to 200 nm thick interpenetrating plates. Furthermore, the microparticles on the surface of the crystals are progressively embedded during the crystal growth. DRMs can be easily isolated and re-dispersed into different solvents. This remarkable capacity to nucleate MOF was shown when DRMs were inoculated into a fresh DEF-based (N,N diethyl formamide) MOF-5 growing medium. This was found to synthesis better quality crystals (SI). The addition of the DRMs doubled the crystal growth rate in DEF compared to a control solution.

1.2 Using DRMs as Crystallisation Facilitators on Substrates

Experimental

DRMs suspension was dropped on an $Al_2O_3$ substrate and the solvent dried under vacuum to create a continuous bed of DRMs. The substrate was then broken in two halves cutting it along a diameter of the circular DRMs layer. One of the substrate fragments was immersed in a typical DEF solution for MOF synthesis between 80.5° C. and 107.8° C. After less then 15 hours MOF crystals were detected only in the region covered with microparticles.

Results

Bare alumina surface does not promote MOF formation. However, in the substrate in which a bed of DRMs was deposited on the alumina substrate MOF crystal grew exclusively on the microspheres on the alumina. The MOF crystals were subsequently harvested from the surface.

Figure 5:
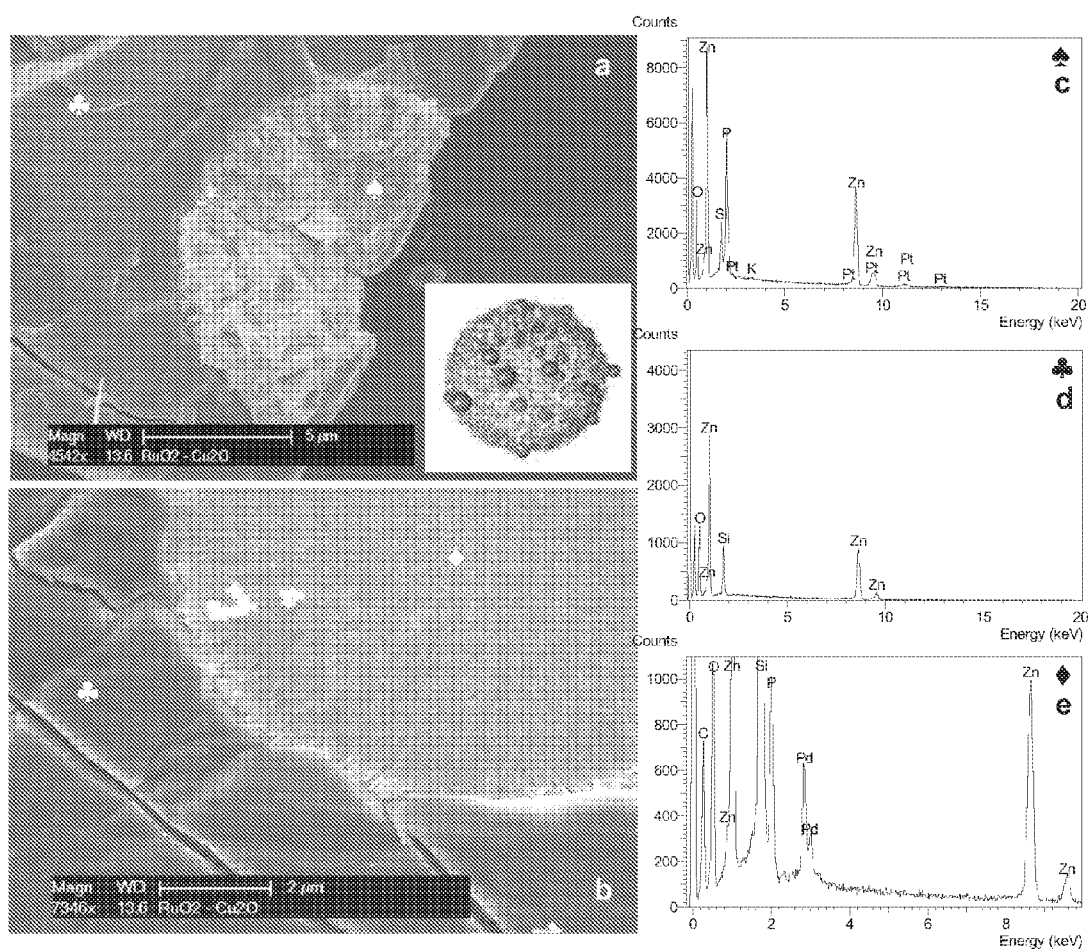
FIG. 5 provides a diagrammatic representation, elemental analyses and SEM images of metal organic framework crystal growth with crystallisation facilitator according to one embodiment of the present invention creating a host-guest system to embed functional species inside the metal-organic crystals, especially using a one pot synthesis.

The SEM images in FIG. 5 show both halves of the original $Al_2O_3$ substrate for comparison purposes. The low magnification image at the top (FIG. 5(a)) makes it easy to recognise the circular shape of the starting DRMs bed, formed after the solvent evaporation. The bottom image (FIG. 5(b)) gives a zoomed view of the cut substrate. The right portion of both images shows the substrate that had not been immersed in the MOF-5 growing medium, which was kept to get a representation of the DRMs bed. The left side shows the substrate portion that had been used to promote MOF formation, and it shows that MOF-5 cubic crystals have formed exclusively on the DRMs bed.

The optical microscope images shown in FIG. 3 show that truncated MOF crystals are formed on the substrate. An analysis of each detached crystal showed that several DRMs are detectable inside that MOF crystals structure, all lying on the crystal face that grew in contact with the DRM seeded surface. Both the crystal shape and the embedded microparticles reveal the heterogeneous character and preferential growth direction of the DRM-promoted crystallisation promoting mechanism. Similar processes were used to induce the growth of inorganic crystals on polymer nanoparticles for bio-mineralization purposes. The experiment highlights the ability of the zinc-phosphate microparticles to nucleate MOF-5 crystals in different solvents and substrates.

This experiment illustrates the crystallisation promoting capability of the DRMs to enable MOF crystal formation on a variety of substrates.

1.3 Lithography Combined with DRMs

Experimental

A special substrate was fabricated by means of X-ray lithography on a SU-8 membrane to show the potential applicability of DRMs to spatially drive MOF formation. The intention was to create arbitrary patterns of wells to be filled with DRMs, which would eventually be used as a modified substrate for MOF-5 growth.

A SU-8 100 membrane (Microchem Corp) is a negative tone epoxy resin membrane widely used in microfabrication. This membrane was chosen due to its excellent chemical resilience to harsh environments, like hot DEF.

A concentrated suspension of DRMs in DMF was prepared by means of centrifugation and washing cycles, as described above. The lithographed substrates were fixed under an optical microsope to allow for precise observation of the procedure of filling the holes in the substrate by dropping the microparticle solution.

The substrates have then been dried under vacuum for 5 hours, and eventually immersed into a standard DEF-based MOF-5 growing solution.

Results

Figure 4:
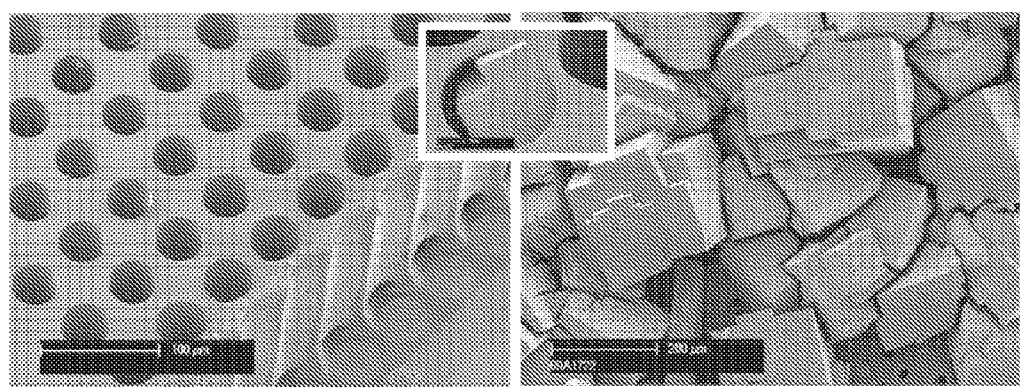
FIG. 4 provides optical microscope images of different zones of a lithographed mask before and after seeding with crystallisation facilitator and growing MOF-5.

FIG. 4 shows the effect of DRMs captured in 30-50 μm diameter channels of a 100 μm thick patterned SU-8 resist. The lithographed substrate was seeded with an average of one DRM microparticle per hole and they were then immersed in a solution for MOF-5 growth. The SEM images in FIG. 4 depict the MOF growth with time. It can be seen that the MOF crystals nucleate inside the wells, and are constrained in size until they continue to grow out of the wells, where they can freely increase their size in all directions. The system evolves towards the formation of an interpenetrated crystalline structure merging the MOF crystals together. The growth proceeds in both the directions along the channel axis, and after less than 15 hours the resist can be detached from the silicon wafer to form a self standing membrane with the channels occupied by MOF.

This lithographic process allows selective MOF growth in customized deep channels. This concept opens new frontiers to customize and control architectures to produce complex microdevices taking advantage of the appealing properties of MOFs.

1.4 Embedding Functional Particles in a MOF—Pt and Pd Nanoparticles

Figure 8:
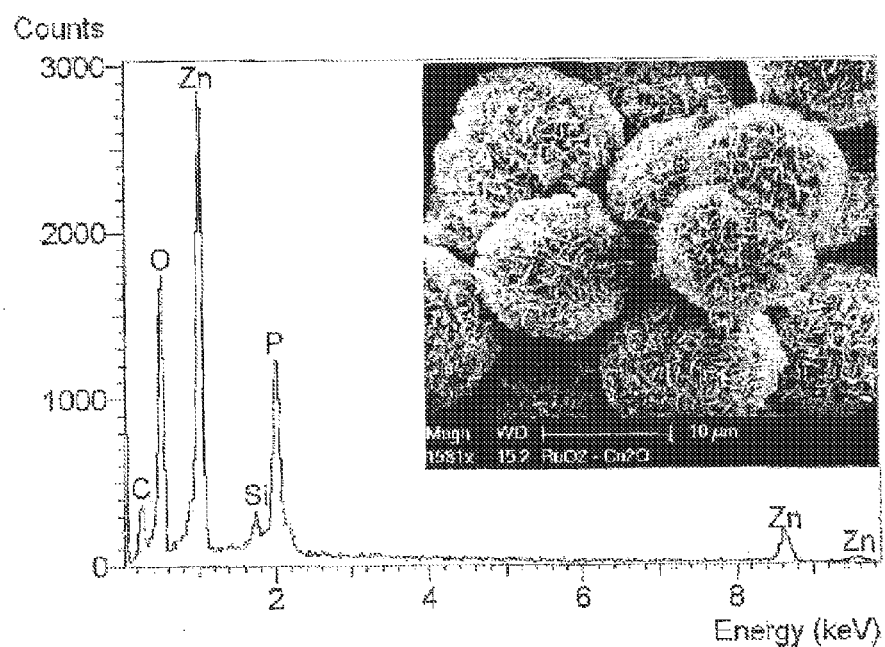
FIG. 8 provides X-ray emissions of atomic species belonging to the crystallisation facilitator shown in the inset.

The following experiment shows that DRMs crystallisation promoting particles can be used as a vehicle to create a host-guest system as depicted in FIG. 8 to embed functional species inside the metal-organic crystals, especially using a one pot synthesis.

Experimental

Pt and Pd nanoparticles, 30 nm and 130 nm diameter respectively, were separately synthesized and added to the solution in which DRMs are growing. Pt and Pd nanoparticles were chosen for the potential synergistic properties that could arise if combined with MOFs (e.g., highly selective catalysts, specific antitumor agents, hydrogen storage systems). These DRMs were subsequently added to a DEF-based MOF growing medium.

Results

In both the one-pot and the inoculation-triggered synthesis, the observed kinetics of MOF-5 growth showed no appreciable change if compared to the synthesis without metal nanoparticles. As shown in FIG. 5, an elemental analysis of the sectioned crystals confirmed the presence of platinum and palladium species in the microparticles. No signal of the noble metals was recorded in the MOF.

The proposed synthesis can be performed with the simultaneous advantages of an easy one-step process that nucleates MOFs allowing for spatial control of the noble metal location in the crystal. This method represents a promising way to synthesize a new generation of host-guest MOF system with a heart of active material surrounded by a molecular sieve.

1.5 Embedding Functional Particles in a MOF—Polymeric Particles

Figure 5A:
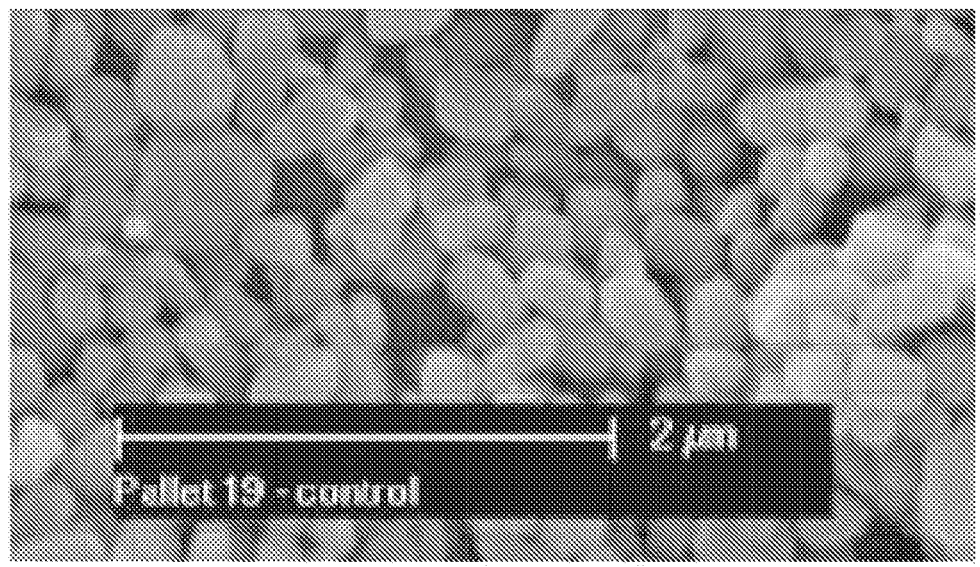
FIG. 5A shows a SEM micrograph showing PTFE nanoparticles which can be embedded in a metal organic framework according to one embodiment of the present invention.
Figure 5B:
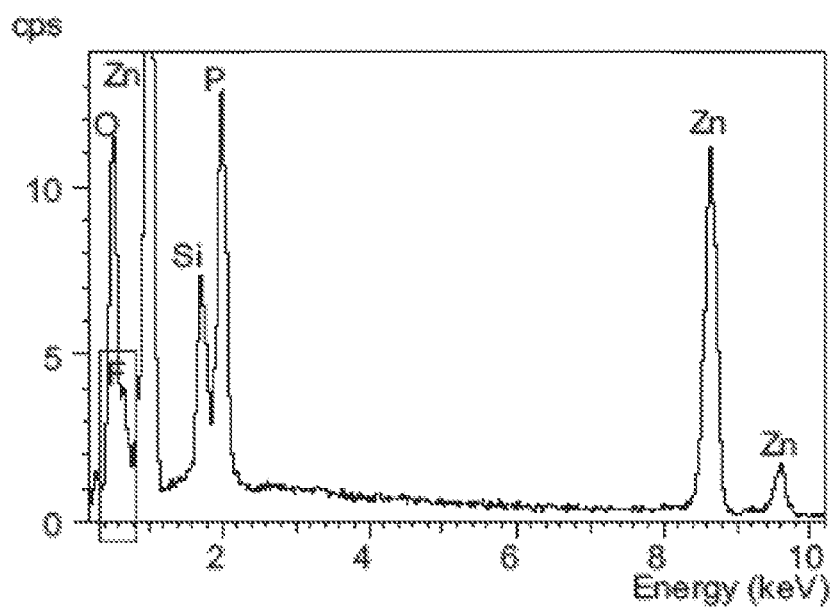
FIG. 5B shows an EDX spectra performed on sectioned desert rose microparticle containing polymer nanoparticles. The Fluorine signal is highlighted in the Figure.

PTFE nanoparticles were also used as a polymeric functional species which could be embedded inside a metal-organic crystals, in this case MOF-5, In a similar method as described above for Pd and Pt nanoparticles, Desert Rose Microparticles (DRM as described in the previous examples) were synthesized in presence of PTFE particles (examples of which are shown in FIG. 5A). The functionalized DRM were then used to nucleate MOFs in a one- or two-step synthesis using a typical MOF-5 growing medium using a similar method as previously described. The following reagents and operative conditions were used:

$Zn(NO_3)_2$=0.377 g

Terephthalic acid=0.043 g

Diemethylformamide=10 mL

Pluronic F127=0.4 g

PTFE nanoparticles=20 mg
Operative Conditions:
Oil Bath 100° C.
Reaction time=20 hours The resulting MOF crystals appeared to surround the functionalized DRM. A MOF-5 crystal containing the functionalised DRM was sectioned and an electron beam pointed on the DRM to provide an EDX spectra shown in FIG. 5B. The emission from fluorine can be clearly detected, as shown in the highlighted section of FIG. 5B indicating the presence of the fluropolymer within the DRM and MOF-5 crystal structure.

1.6 Characterisation of the Desert Rose Microparticles (DRMs)

The chemical structure of the desert-rose microparticles (DRMs) were analysed using FTIR. The sample consisted of dried DRMs collected by centrifugation after three hours reaction of a typical Pluronic-based MOF-5 growing medium around 100° C. The DRMs powder was washed with fresh DMF first, followed by fresh dichloromethane and eventually dried under a nitrogen flux.

Figure 6:
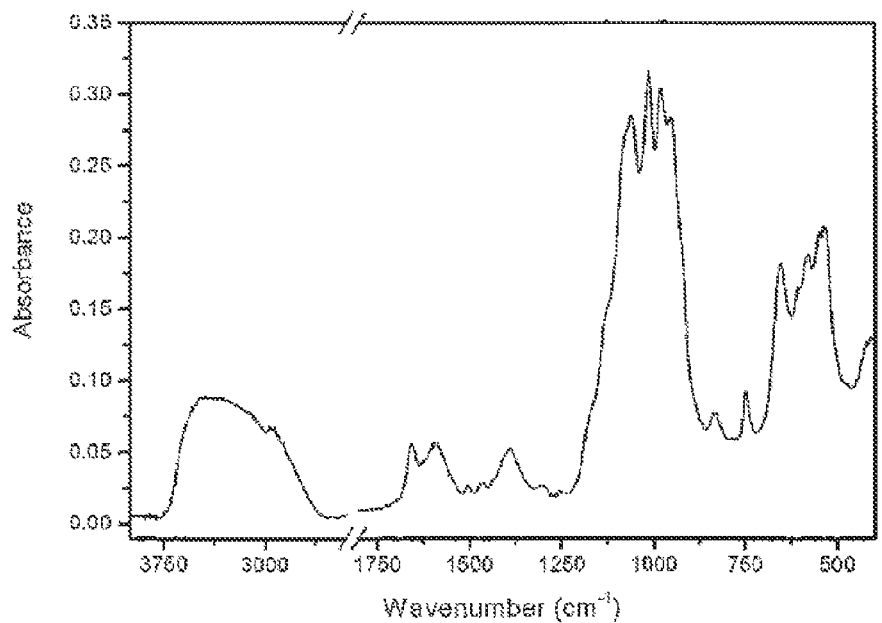
FIG. 6 provides an FTIR absorption spectrum measured on a dry powder of isolated particles of crystallisation facilitator according to one embodiment of the present invention.

The features of the FTIR absorption spectrum shown in FIG. 6 are associated to the main vibration modes of zinc phosphates. In particular, the detected signals are in their majority consistent with the chemical structure of α-hopeite, $Zn_3(PO_4)_2.4H_2O$. The v1, v3 and v4 modes of the tetrahedron phosphate centers were clearly identified. The intense broad band in the 3000 to 3600 $cm^{-1}$ region confirms the hydration state of the zinc phosphate compound. Signals from terephthalic acid inclusions and residual solvent DMF can be detected respectively at 1300 to 1600 $cm^{-1}$ and 2860 to 2970 $cm^{-1}$.

Figure 7:
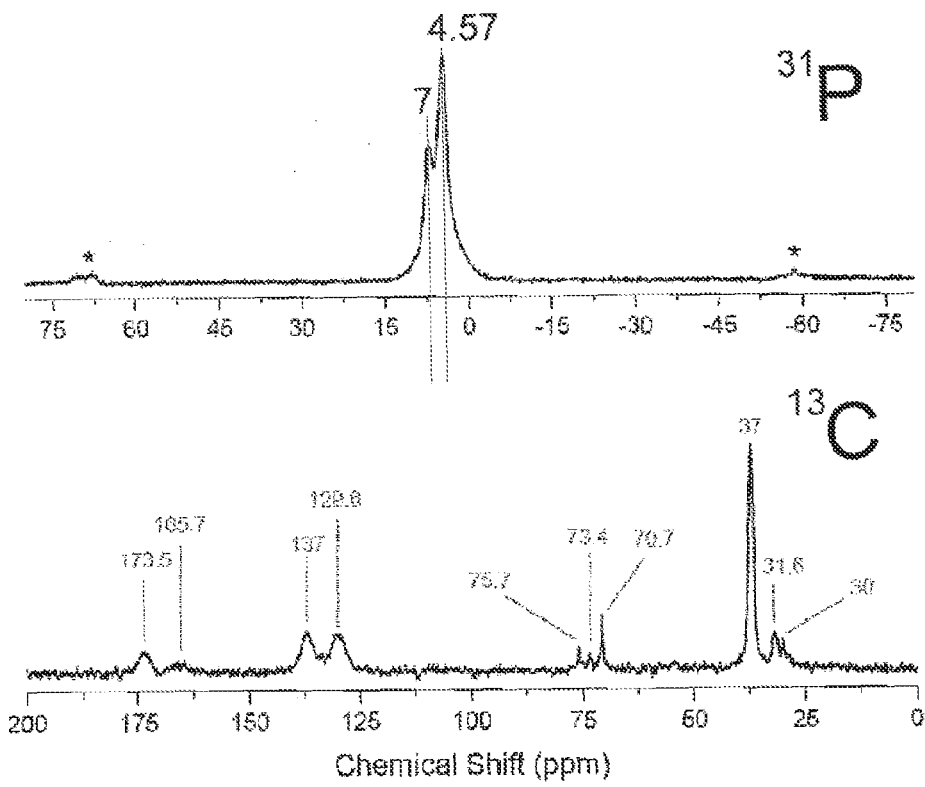
FIG. 7 provides $^{13}$C and $^{31}$P NMR spectra of dried powder comprising a crystallisation facilitator according to one embodiment of the present invention.

Samples of dried DRMs used for FTIR underwent $^{13}C$ and $^{31}P$ NMR characterization. The plots are reported in FIG. 7.

The $^{31}P$ NMR spectrum shows a composite band centered at 4.57 (first peak, α-hopeite) ppm and 7 ppm (second peak, hydrogen-phosphate $Zn_x(HPO_4)_x$ species or effect of DMF molecules that substitute water in the Zn centres of α-hopeite).

Carbon $^{13}C$ NMR revealed presence of residuals from the organic precursors used in the synthesis of MOF-5, and of the DMF solvent. The observed shifts and their association are listed in Table 1.

TABLE 1

$^{13}C$ NMR Chemical shifts and associated molecules in dried DRMs.

| Chemical Shift (ppm) | Molecule |
|---|---|
| 173.5 | Terephthalic |
| 137 | Acid |
| 129.6 | |
| 30 | |
| 75.7 | Pluronic |
| 73.4 | F-127 |
| 70.7 | |
| 165.7 | DMF |
| 37 | |
| 31.6 | |

The molecules' association was made running $^{13}C$ NMR spectra of each single precursor and solvent used in the reaction batch. $^{13}C$ NMR of the DRMs shows inclusions of some of them in the DRMs structure. Along with the $^{31}P$ spectrum and the FTIR analysis, $^{13}C$ NMR further enforces the hypothesis of the inorganic nature of DRMs. The high intensity of the 37 ppm peak is associated to the strong interaction between DMF molecules and the zinc centers in the DRMs structure, which can be traced also in the $^{31}P$ NMR of FIG. 7.

The analysis of the atomic species forming the DRMs chemical structure was performed by means of the EDAX FIG. 8 reports the resulting X ray emission plot with an inset image of the actual portion of sample that was analyzed. Fingerprints of Kα and Lα emissions of Zn, C and P are detected. Si signal is mainly form the substrate.

The low intensity of the carbon emission confirms again the mostly inorganic nature of the DRMs. This is further reinforced considering that the carbon coating also contributes to the observed emission. Zn, P and O signals are consistent with the chemical structure of α-hopeite.

Example 2

Metal Chalcogenide Nanoparticles 2.1. $SiO_2$ Nanoparticles

In this aspect of the present invention, several batches of $SiO_2$ nanoparticles (nanoparticles) were synthesized using a modified Stöber approach. Beside pure $SiO_2$ nanoparticles, suspensions with chemically modified nanoparticles have been realised by adding functional amino-, carboxy- and hydroxy-groups to the main $SiO_2$ network by means of suitable sol-gel precursors. FTIR analysis of dried nanoparticle powders confirmed the presence of such functional groups within the $SiO_2$ network. The studied crystallisation facilitators are $SiO_2$ nanoparticles, though it should be appreciated that other metal oxide compounds may also be suitable.

In the experiments, MOF-5 was used as an example of a metal organic framework that can be grown using the crystallisation facilitators of the present invention. MOF-5 is one of the most studied metal organic frameworks and it was a benchmark material for proving numerous concepts and properties. It should be understood that MOF-5 was used for example purposes only, and that a large variety of other metal organic frameworks could be formed using the below described techniques.

Experimental

Tetraethoxysilane (TEOS), aminopropyl triethoxysilane (APTES), vinyl trimethoxysilane (VTES), fluorescinisothiocyanate (FITC), zinc nitrate hexahydrate, 1,4-benzenecarboxylic acid (BCA), diethylformamide (DEF) and dimethylformamide (DMF) were purchased from Aldrich and used without further purification. Functional $SiO_2$ nanoparticles were synthesized using a modified Sol-Gel Stöber approach (according to C J. Brinker, G. W. Scherer, *Sol-Gel Science: the Physics and Chemistry of Sol-Gel Processing*, Academic Press Inc., 1989). A suitable alkoxy-silane precursor was added to the main reaction batch, to obtain nanoparticles with different chemical functionality. Particles with -amino, -carboxy and -hydroxy functional groups have been obtained using APTES, oxidized VTES and FITC respectively.

$SiO_2$particles: TEOS (0.1 to 10 mL) was first dissolved in Ethanol (EtOH, 0.1 to 100 mL), and subsequently a 25% ammonia solution (1 to 30 mL) was added dropwise under continuous and vigorous stirring. After 60 to 300 minutes the solution started to assume an opalescent tone due to scattering from the forming $SiO_2$ nanoparticles. The mixture was kept under stirring overnight to allow for complete reaction of the precursors. The suspended particles were centrifuged, vacuum dried and re-suspended in fresh EtOH.

The washing procedure was repeated four times and the particles have eventually been stored as a dry white powder. The whole procedure was performed at room temperature and humidity.

$SiO_2$—$NH_2$ particles: TEOS (0.1 to 50 mL) and APTES (0.01 to 10 mL) were first dissolved in EtOH (0.1 to 100 mL). Subsequently, a 25% ammonia solution (0.1 to 75 mL) was added dropwise under continuous and vigorous stirring. The mixture was allowed to react overnight and the particles eventually washed according to the same procedure described above. The particles were stored as a white dry powder.

$SiO_2$—COOH particles: TEOS (0.1 to 50 mL) and VTES (0.01 to 75 mL) were initially dissolved in EtOH (0.01 to 100 mL). Subsequently, a 25% ammonia solution (0.1 to 75 mL) was added dropwise under continuous and vigorous stirring. The mixture was allowed to react overnight and the particles eventually washed as described above. The vinyl-terminations of VTES were then oxidized to carboxy-functions by suspending the particles into an aqueous solution (0.1 to 100 mL) of $KMnO_4$ (0.1 to 15 mg) and $NaIO_4$ (0.1 to 500 mg) for 12 hours, according to a protocol described by Wasserman and co-workers (S. R. Wasserman, Y. T. Tao, G. M. Whitesides, *Langmuir* 1989, 5, 1074-1087). Again, the colloids have been separated by centrifugation and washed twice with distilled water and EtOH.

$SiO_2$—OH particles: some of the $SiO_2$—$NH_2$ nanoparticles were suspended in a solution of FITC (0.1 to 15 mg) in EtOH (0.1 to 100 mL). The iso-thiocyanate termination of the FTIC molecules condensed with the amino-functions of the nanoparticles, exposing the hydroxy-terminations of the FTIC molecules to the solvent. The particles were kept suspended in the FTIC solution for 20 to 120 minutes, then were centrifuged and washed in fresh EtOH, to be finally vacuum-dried and stored as an orange powder.

Solvothermal growth of MOF-5 in presence of $SiO_2$ nanoparticles: MOF-5 crystals were synthesized using a typical solvo-thermal approach. A mother batch of precursors was first made by dissolving $Zn(NO_3)_2$ (0.01 to 5 g) and BCA (0.01 to 20 g) in DEF (1 to 150 mL). The resulting solution was then divided into 1 to 5 mL aliquots, one for each of the surface modified nanoparticle types, plus a control (five aliquots in total). $SiO_2$ nanoparticles with different functionalities were added to each one of the aliquots and suspended in an ultrasonic bath. No particles were added to the control solution. The vials were Teflon-sealed and heated at 75° C. to 130° C. under constant stirring for up to 10 to 48 hours.

MOF-5 growth on a bed of $SiO_2$ nanoparticles: a circular bed of $SiO_2$—COOH nanoparticles was formed on a silicon wafer by drop-casting a concentrated nanoparticle suspension in EtOH, which was subsequently vacuum dried. The modified silicon substrate was then immersed into a MOF-5 precursor solution obtained according to the procedure described above, with the only difference that DMF was used as the solvent instead of DEF. The batch was then Teflon-sealed and immersed into an oil bath previously heated at 65° C. to 110° C. The substrates have then been extracted, rinsed with fresh DMF and vacuum-dried prior to further analysis.

Results

Figure 9:
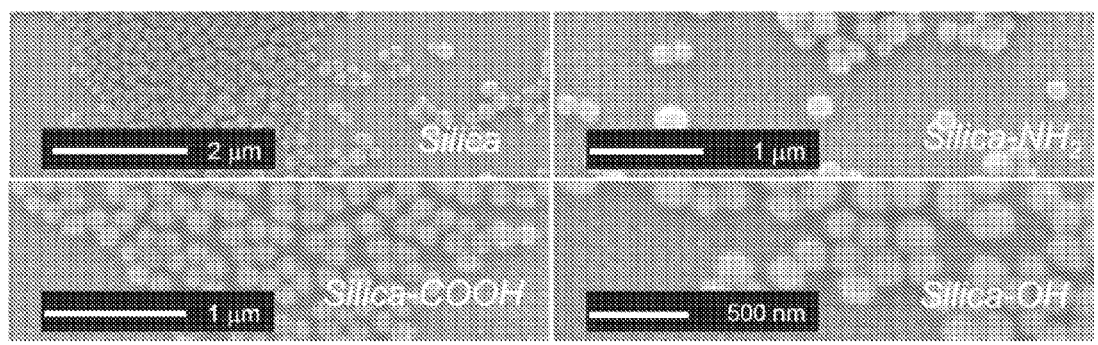
FIG. 9 provides SEM images of SiO$_2$ nanoparticles synthesized integrating functional alkoxysilanes in a conventional Stöber approach to provide a crystallisation facilitator according to another embodiment of the present invention. The images refer to batches of (a) SiO$_2$, (b) amino-functionalised SiO$_2$, (c) carboxy-functionalised SiO$_2$ and (d) hydroxyl functionalised SiO$_2$.

SEM images of FIG. 9 show the $SiO_2$ nanoparticles that were synthesized using a standard Stöber protocol (FIG. 9.*a*) together with those with customised composition (FIGS. 9.*b*, 9.*c*, 9.*d*). The particles have subsequently been suspended in several MOF-5 growing media containing zinc nitrate and terephthalic acid dissolved in N,N-diethylformamide (DEF). All the solutions underwent sonication until completely transparent. The formation of MOF crystals was promoted by heating the batches according to the usual solvothermal procedure adopted for the synthesis of MOF-5.

The resulting suspensions appeared perfectly transparent, and did not assume the typical opalescent appearance of $SiO_2$ nanoparticles suspensions in EtOH. The vials with the suspensions were then inserted into an oil heated holder and kept under constant stirring. After two hours of reaction, the growing media containing $SiO_2$—COOH and $SiO_2$—$NH_2$ nanoparticles showed an obvious decrease in transparency as a thick suspension starts to form. An aliquot from each of these samples was taken and characterised with SEM. At this reaction stage, micron size MOF crystals are easily observed (images in FIG. 12.*a*, 12.*b*, 12.*c*). The images give an insight into interaction between nanoparticles and forming MOF, as the nanoparticles are clearly embedded, or in the process of being embedded, inside the crystals framework. Together with the very short reaction timeframe until this point, this is a first evidence of a promoting effect of the functionalised nanoparticles in the formation of MOF-5 micro-crystals. No crystal formation was observed in the control or in the batches containing pure $SiO_2$ and $SiO_2$—OH nanoparticles.

Figure 10:
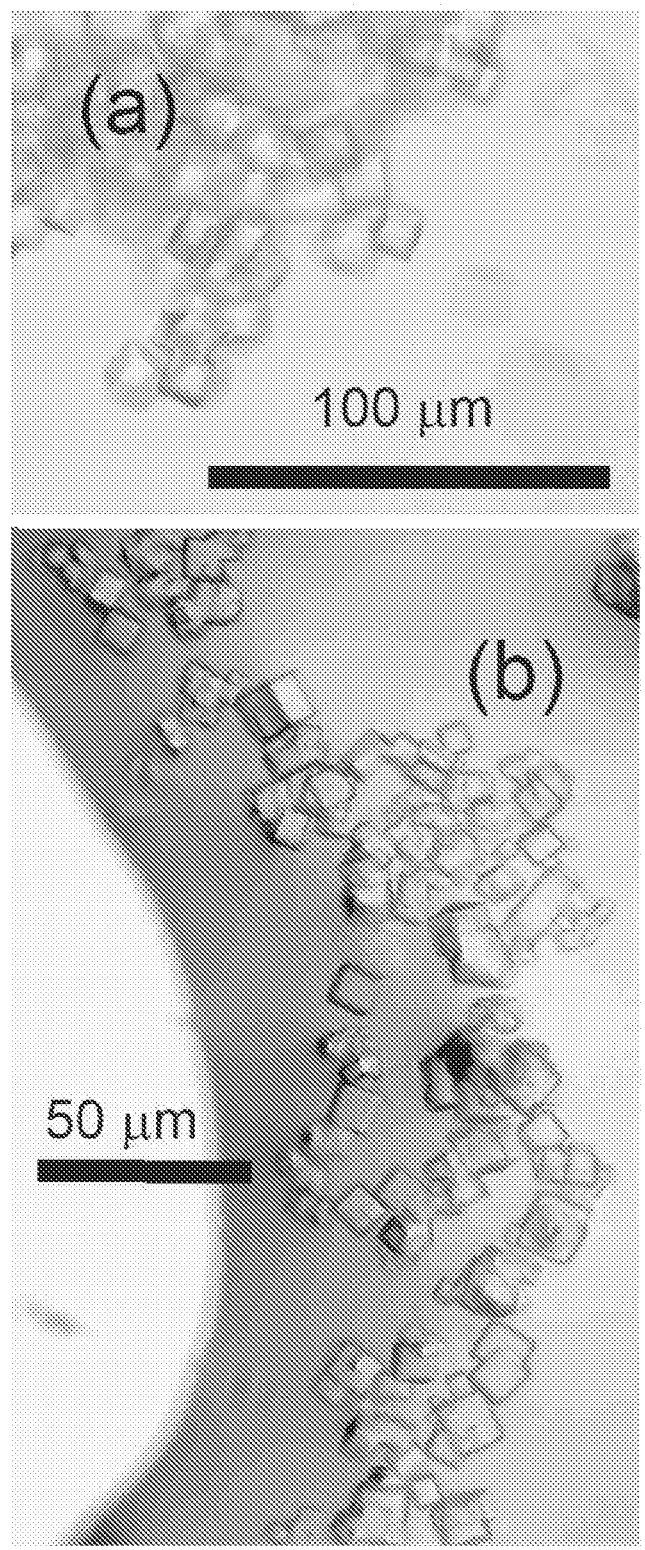
FIG. 10 provides optical microscope images of cubic crystals formed after 10 hours reaction at 95° C. formed in MOF-5 growing media containing (a) SiO$_2$—COOH and (b) SiO$_2$—NH$_2$ nanoparticles.

Further aliquots were been extracted and characterized with an optical microscope (FIG. 10). The optical microscopy images of FIG. 10 reveal the presence of cubic crystals formed in the solution containing $SiO_2$—COOH and $SiO_2$—$NH_2$ nanoparticles. No trace of cubic crystals was observed in the control solution or in those containing $SiO_2$ and $SiO_2$—OH nanoparticles. The narrow distribution of the crystals size, the high number of crystals formed and their reduced size are indicative of a nucleation driven process. This is particularly evident in presence of the -carboxy modified nanoparticles, in which the crystals' size distribution is well below the monodispersion threshold.

Figure 11:
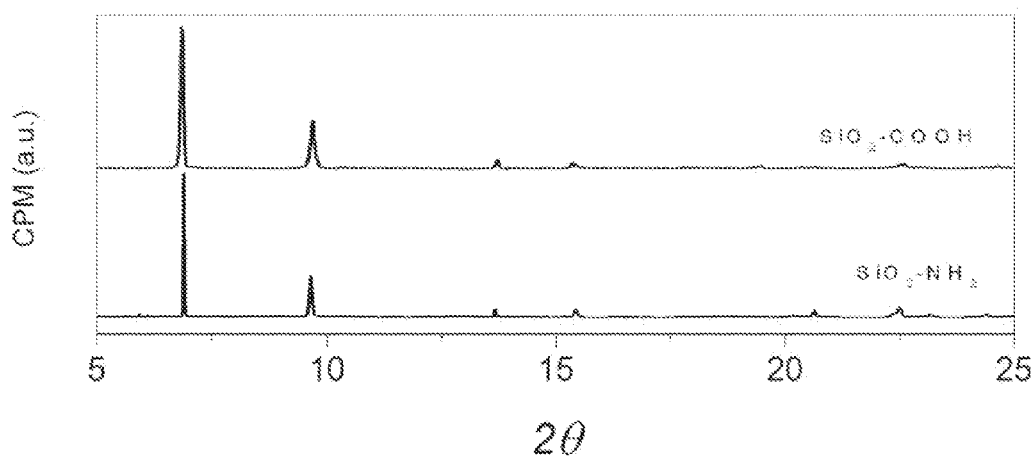
FIG. 11 provides X-ray diffraction patterns of MOF-5 crystals grown in presence of (a) SiO$_2$—COOH and (b) SiO$_2$—NH$_2$ nanoparticles.

X-ray diffractometry of dried crystals was performed using a Powder Diffraction beamline of a synchrotron. FIG. 11 reports the diffraction patterns of the crystals obtained adding $SiO_2$—COOH and $SiO_2$—$NH_2$ nanoparticles to the MOF-5 precursors' solution. The pattern is consistent with the pattern reported for MOF-5 (see for example O. M. Yaghi, M. Eddaoudi, H. Li, J. Kim, N. Rosi, in international patent application WO 02/088148). The main diffraction peaks at low angles, at 6.9° (<200>) plane, d=12.8 Å) and 9.7° (<220>) plane, d=9.1 Å), are indicative of the modular arrangement of large pores in the MOF-5 cubic lattice.

Figure 12:
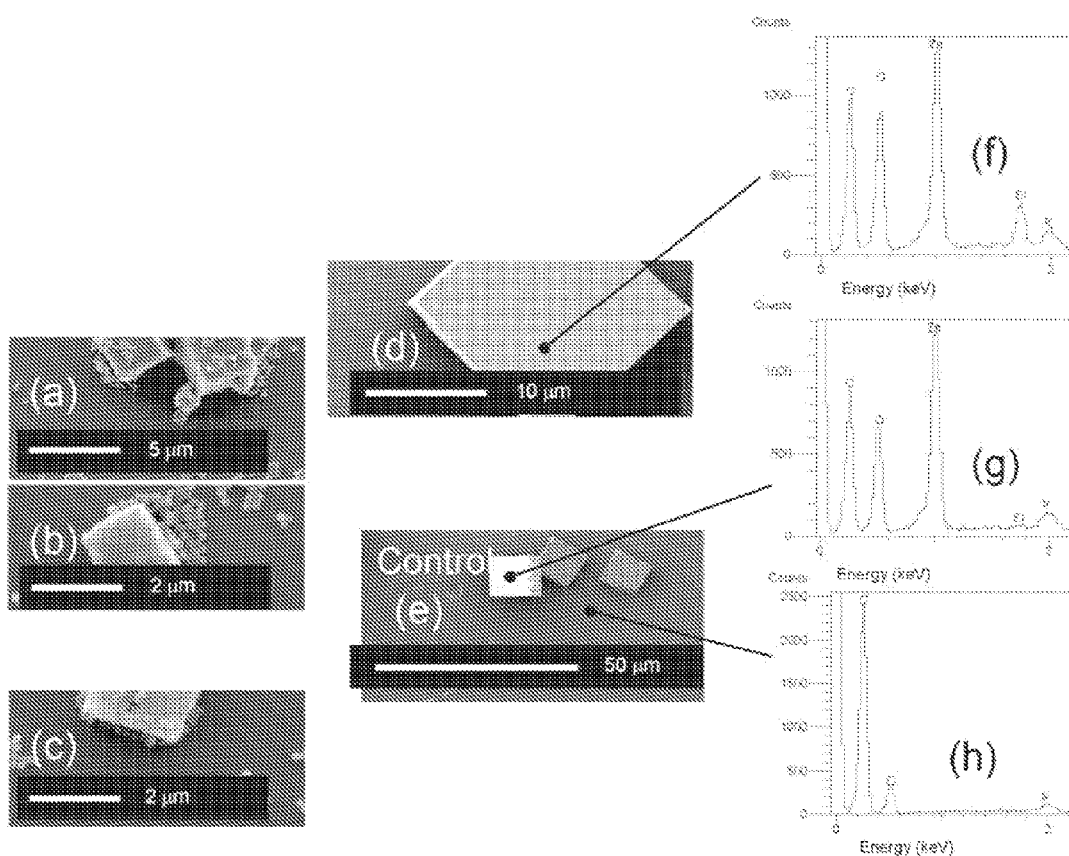
FIG. 12 provides SEM images of MOF-5 crystals formed in a solution containing SiO$_2$—COOH nanoparticles after 4 hours reaction (a, b, c) and after 10 hours reaction (d). Image 4(e) refers to MOF-5 crystals formed in the control solution (no nanoparticles) in 60 hours.

FIG. 12 shows SEM images of MOF-5 crystals in presence of $SiO_2$—COOH nanoparticles, together with an image of MOF-5 crystals of similar size collected from the control solution (12.*e*). The samples for imaging have been prepared by fixing dry crystals onto the surface of double-sided carbon conductive tape (SPI supplies), and then coating them with an Iridium layer. The plots of FIGS. 12.*f*, 12.*g* and 12.*h* are the Energy Dispersive X-ray (EDAX) signals recorded after scanning a portion of a nanoparticle-generated crystal, a control crystal and the background tape respectively. Images of FIGS. 12.*a*, 12.*b* and 12.*c* were collected without filtering the crystals from the nanoparticle suspension; it is in fact clear from the images that several nanoparticles are embedded into the forming cubic network. Both the EDAX plots obtained scanning a Nanoparticles-formed crystal (12.*f*) and a control crystal (12.*g*) show distinctive emissions of the MOF-5 components, Carbon Kα (0.277 keV), Oxygen Kα (0.523 keV) and Zinc Lα (1.012 keV). The plot in 12.*f* also shows the distinctive Kα emission of Silicon (1.74 keV). The background emission (12.*h*) is dominated by C—Kα and O—Kα radiations. In all the samples the Iridium coating contributes with its Mα emission at 1.978 keV.

SEM imaging and EDAX analysis (FIG. 12.f, 12.g, 12.h) further strengthen what is stated above. In fact, they highlight the enclosure of the nanoparticles within the MOF framework, again demonstrating the chemical affinity of the two components. In the case of no chemical interaction, the crystals would have grown in the usual fashion without incorporating the nanoparticles inside the structure. X-ray diffraction measurements give a set of information which extends beyond the mere confirmation that the observed crystals are indeed MOF-5. As an archetype of a typical MOF structure, MOF-5 was synthesized in a variety of methods, and characterized in extreme detail in countless publications. Hafizovic and co-workers (J. Hafizovic, M. Bjørgen, U. Olsbye, P. D. C. Dietzel, S. Bordiga, C. Prestipino, C. Lamberti, K. P. Lillerud, J. Am. Chem. Soc. 2007, 129, 3612-3620) found and confirmed important qualitative correlations between the XRD plots generated by MOF-5 samples and their crystalline quality; their study aimed to explain the wide range of MOF-5 specific surface values reported in literature. It was found that the relative intensity of the 6.9° and 9.7° diffraction signals are strongly affected by the presence of lattice defects, adsorbed species (solvent molecules included) and unreacted Zn centres. As those peaks are the direct evidence of the large MOF-5 pores' arrangements, the Authors outlined a qualitative relationship between the diffraction plots and the structural quality of MOF-5. Under this perspective, the measured diffraction plots of FIG. 11 show the typical features of high quality and noninterpenetrated MOF-5 crystals.

After observing the seeding effect in solution, the crystal promoting capability of the modified $SiO_2$ nanoparticles has also been tested on flat silicon substrates, which are known to be unfavourable growing supports for MOF-5. Here, $SiO_2$—COOH modified nanoparticles were used to show the seeding effect of dry nanoparticles for the production of MOF-5 crystals on 2D surfaces which does not usually promote MOF formation. A nanoparticles bed on a silicon wafer was used as growing media for MOF-5, and the resulting sample was chemically characterised using FTIR. In addition, to further extend the method's potentiality the conventional MOF-5 growing medium was synthesized using Dimethylformamide (DMF) instead of Diethylformamide (DEF), which is an appealing choice from an industrial prospective given the remarkable lower cost of DMF. $SiO_2$—COOH nanoparticles had been selected as the preferred candidates given their superior seeding performance in suspension.

Figure 13:
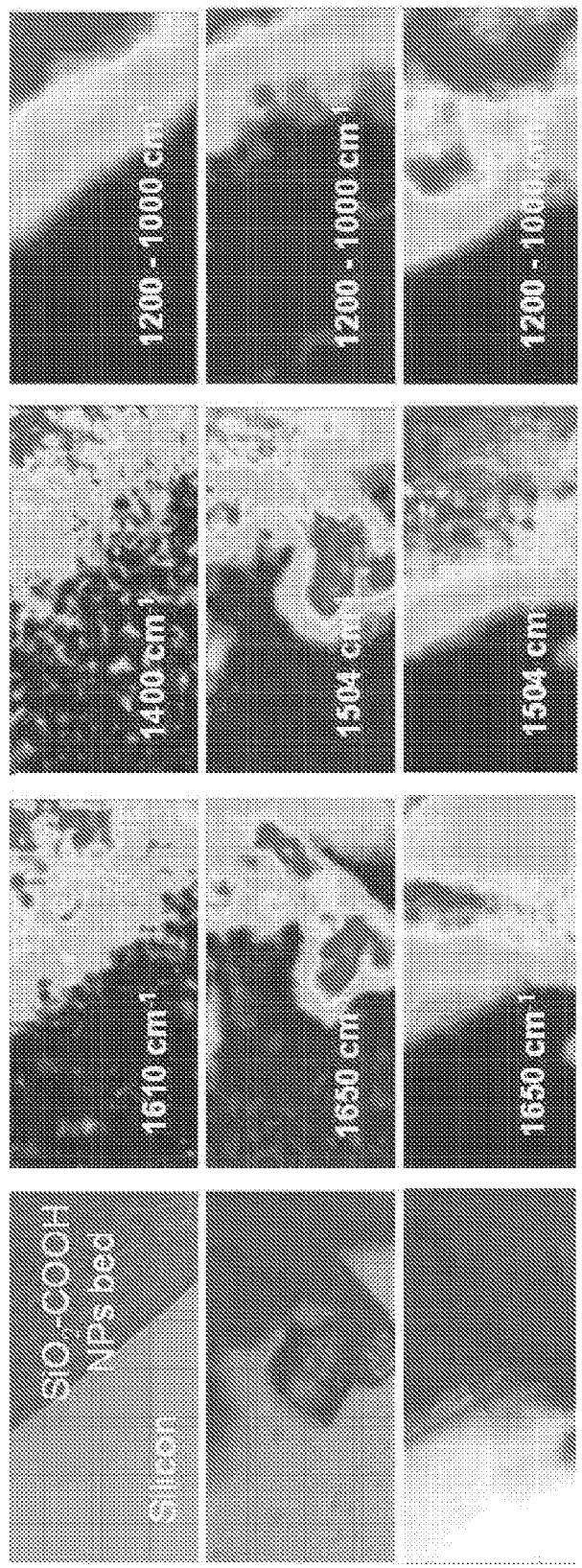
FIG. 13 provides optical images and 2D FTIR chemical maps of MOF-5 crystals grown locally on a SiO$_2$—COOH nanoparticle bed dried on a silicon surface.

FIG. 13 shows 2D FTIR maps collected initially on the —COOH modified nanoparticle bed, and then on the same substrate after MOF-5 growth. Each row reports an optical image of the sampling area and its relative chemical maps. The top line of images refers to measurements on the nanoparticle bed before MOF-5 growth, emphasizing the absorption from the $SiO_2$ network and from the un-coordinated carboxy-functions. The central and bottom lines of images refer to measurements performed after the growth of the MOF-5 crystals, with an emphasis on the absorption of the coordinated-carboxy functions, the aromatic linkers and the $SiO_2$ nanoparticle bed underneath the MOF-5 formations.

The maps are coupled with an optical image of the sampled area. The upper line of maps show the absorbed IR signal integrated along the characteristic vibration frequencies of the Si—O—Si silica bonds (1200 $cm^{-1}$-1000 $cm^{-1}$) and along the twin frequencies of the antisymmetric OCO ($n_a$oco) stretches of the carboxylic terminations. The central and bottom line of maps have been taken after MOF-5 growth, and report the integrated absorbance of characteristic MOF-5 structural bonds recorded from two different spots of the same sample. The images evidence the presence of the antisymmetric OCO ($n_a$oco) vibrations, shifted at around 1650 $cm^{-1}$, and of the sharp CC double bond symmetric stretch ($n_s$cc) vibrations of the aromatic species. The maps also highlight the location of the nanoparticle bed underneath the grown crystals, as the signal from the silica network (1200 $cm^{-1}$-1000 $cm^{-1}$) is also reported. The spatial arrangement of both the organic and inorganic chemical bonds is consistent with the expected distribution of the analysed species, as it overlaps with the optical microscope images.

The nanoparticle bed dried on the silicon substrate was chemically mapped using FTIR, as shown in the top line images of FIG. 13. The siliceous nature of the seeds was confirmed as well as the chemical state of their carboxy functions. Compared to SAMs, beds of functionalised $SiO_2$ nanoparticles provide a higher concentration of —COOH functions, enough to be detected by transmission FTIR. The twin frequencies of the antisymmetric OCO ($n_a$oco) stretch of the nanoparticles' carboxylic terminations are centred at 1610 $cm^{-1}$ and 1400 $cm^{-1}$. The signal at 1610 $cm^{-1}$ is the typical of de-protonated and un-coordinated O—C—O groups, further confirmed by the absence of the symmetric stretch of C=O bonds (nco) in the 1700 $cm^{-1}$-1750 $cm^{-1}$ region. Given the highly basic synthesis conditions of the nanoparticles, these observations are consistent with reported pKa values for terminal carboxyl functions, which typically sit in the 2.5 to 6 acidic range. Once immersed in the MOF-5 growing medium, the un-protonated carboxyls may facilitate the coordination of $Zn^{2+}$ cations, which in turn allows for the formation of terephthalate bridges connecting the MOF-5 network. The coordination with $Zn^{2+}$ cations is supported by the shift of the main $v_a$ oco frequency component from 1610 $cm^{-1}$ to 1650 $cm^{-1}$, which was measured after the MOF-5 growth. As the OCO band is usually very strong and has almost invariant extinction coefficient (about 1 $mM^{-1} m^{-1}$), it is possible to qualitatively associate its wavenumber shift to the chemical state of the OCO bond. The inductive effects of coordinated metals can be understood in terms of dipole-dipole and charge-dipole interactions, and with a simple empirical consideration a shift of the OCO frequency towards higher frequencies indicates a stabilisation of $COO^-$ species of the TA molecules.

Remarkably, the growing rate of MOF-5 was found to be even faster than that observed using nanoparticles suspended in DEF, as after only 2 hours the modified substrates showed presence of the cubic crystals. FTIR mappings confirmed the chemical nature of the MOF-5. Beside the above mentioned Zn coordinated OCO stretch at 1650 $cm^{-1}$, characteristic symmetric stretch vibrations of the MOF-5 aromatic linkers have been measured at 1504 $cm^{-1}$ (=C—H and ring C=C stretch) and 1015 $cm^{-1}$ (=C—H in coordinated aromatic ring). The chemical maps overlap with the optical images taken from the same sample area with very good approximation, thus facilitating the spatial species recognition.

The modified Stöber protocol reported here allowed for the fast synthesis of highly concentrated $SiO_2$ nanoparticle suspensions. Beside the elevated amount of nanoparticles produced, this approach is appealing from an industrial perspective also for its intrinsic simplicity, time-inexpensiveness and high reaction yield. In addition, the high degree of compositional control makes it possible to produce particles with customised functionality, as shown in the FTIR mappings. The dried nanoparticles were readily dispersed in the MOF-5 growing medium, showing great affinity with DEF.

The described experimental synthesis of $SiO_2$ nanoparticles can easily complement an industrial production line, as it is performed at room temperature, it is cheap, and allows for the production of considerable volume of nanoparticles suspensions in a short time.

The observed dynamics of the $SiO_2$ nanoparticles mediated synthesis of MOF-5 are typical of a nucleation-driven process, resulting in the formation of small crystals with narrow size distribution; at the same time, the proposed synthesis does not rely on the use of growth limiting surface agents. Together, these two aspects are of crucial importance for the development of systems relying on the use of MOFs as building block components for further reaction scale-up or for the engineering of other frameworks.

2.2 $TiO_2$ Beads

Figure 14:
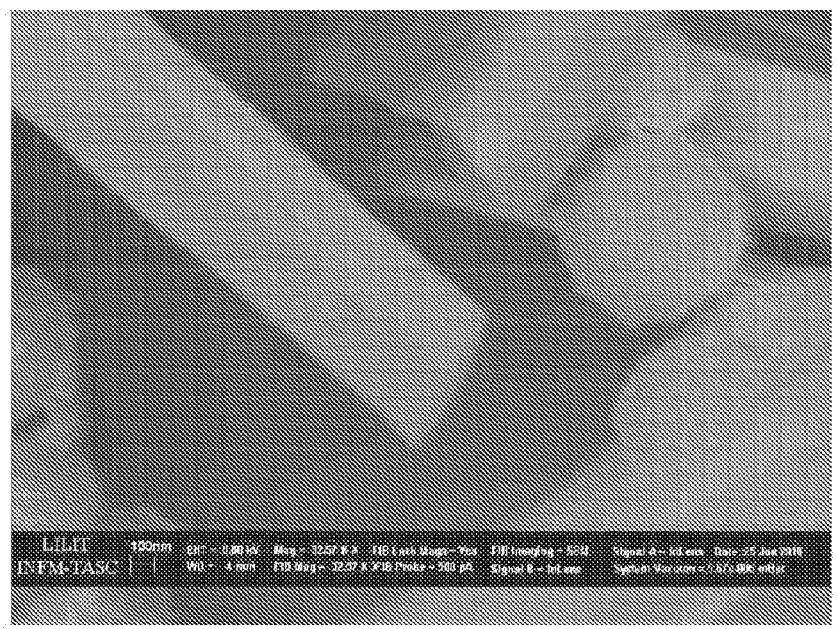
FIG. 14 provides an XRD pattern of a MOF-5 crystal section nucleated using CdSe/CdS/ZnS Quantum Dots crystallisation facilitators according to one embodiment of the present invention (I=1.54 Å).
Figure 15:
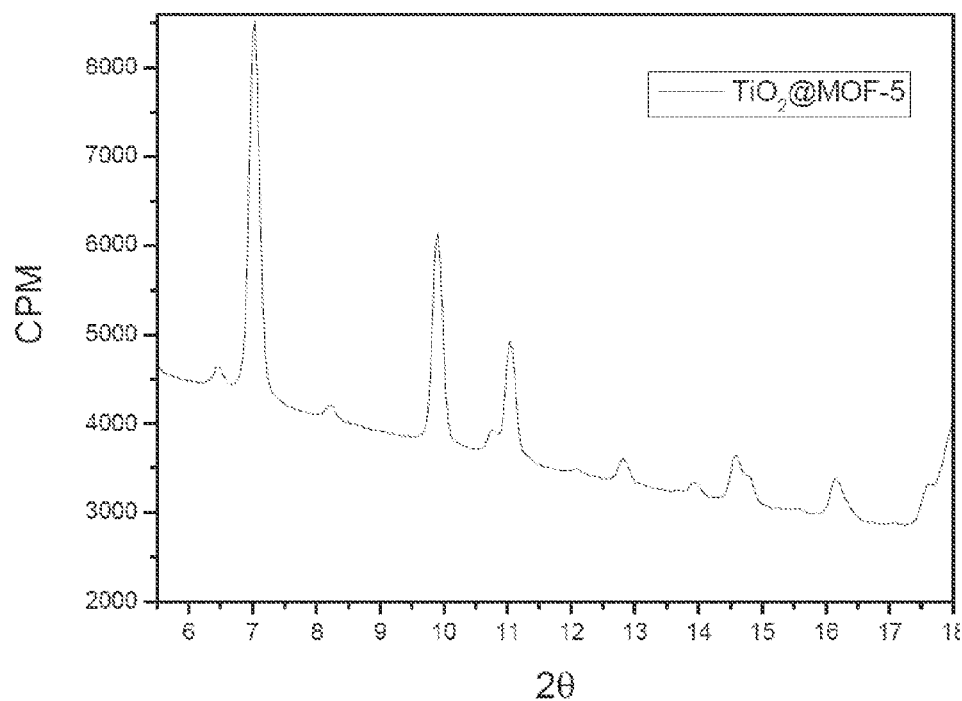
FIG. 15 provides a confocal microscope image of a portion of a MOF-5 crystal section nucleated using CdSe/CdS/ZnS Quantum Dots type crystallisation facilitators according to one embodiment of the present invention. The image shows the 640 nm centred emission of the embedded CdSe/CdS/ZnS Quantum Dots.

Nanometric titania ($TiO_2$) beads were used were used as crystallisation facilitators to nucleate the growth of MOF-5 in solution with an analogue procedure used to nucleate MOF-5 with $SiO_2$ nanoparticles. Nanometric titania ($TiO_2$) beads were introduced into a typical MOF-5 growing medium using a similar method as previously described in section 2.1. The following reagents and operative conditions were used:
 $Zn(NO_3)_2$=0.377 g
 Terephthalic acid=0.043 g
 Diethylformamide=10 mL
 Amino-functionalized $TiO_2$ nanobeads=15 mg
 Operative Conditions:
 Oil Bath 100° C.
 Reaction time=15 hours As shown in the SEM micrograph of FIG. 14, the resulting crystals appear elongated in shape. A Low angle XRD pattern of elongated crystals nucleated by means of amino-functionalized $TiO_2$ beads shown in FIG. 15 show that the diffraction peaks correspond are the ones reported for cubic MOF-5.

2.3 Ferromagnetic Cobalt Nanoparticles 50 nm carbon coated cobalt nanoparticles have been used to were used as crystallisation facilitators to nucleate the growth of MOF-5 in solution using an analogue procedure used to nucleate MOF-5 with $SiO_2$ nanoparticles described previously in section 2.1. Carbon coated cobalt nanoparticles were introduced into a typical MOF-5 growing medium using a similar method as previously described. The following reagents and operative conditions were used:
 MOF-5 mother batch
 $Zn(NO_3)_2$=0.377 g
 Terephthalic acid=0.043 g
 Diethylformamide=10 mL
 Reaction Batches
 1.75 mL Mother Batch+3 mg Co nanoparticles
 1.75 mL Mother Batch+3 mg Co nanoparticles+0.2 g Pluronic F127
 1.75 mL Mother Batch+4 mg Co nanoparticles
 1.75 mL Mother Batch+4 mg Co nanoparticles+0.2 g Pluronic F127

Surfactants could also be added to the precursors in order to change nanoparticle distribution and concentration.

Figure 16:
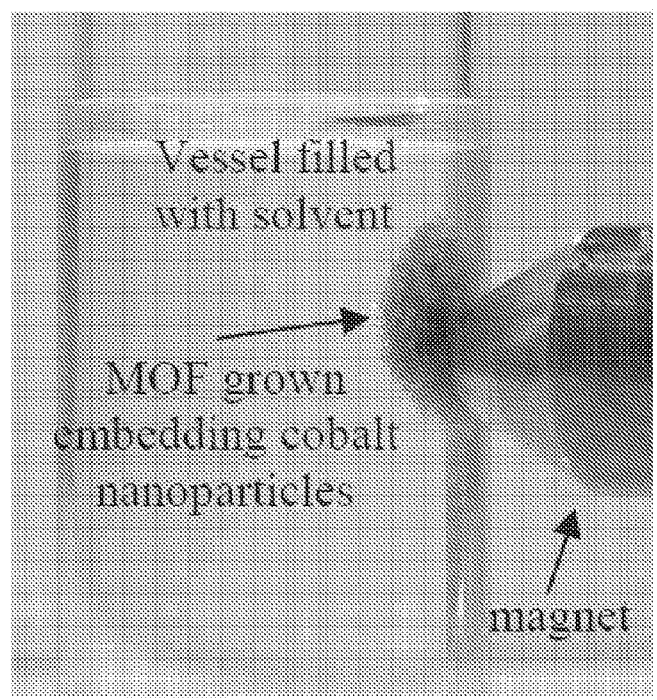
FIG. 16 provides a digital camera image of a magnet tip (right) attracting Co@MOF-5 crystals and holding them suspended on the side of a glass vial.

The resulting crystals show the same ferromagnetic properties as the nanoparticles seeds. They respond to external magnetic fields and their spatial location can be arbitrarily changed by means of common magnets as shown in the FIG. 16 where a magnet tip (right) attracts the Co@MOF-5 crystals and holds these MOF-5 crystals suspended on the side of a glass vial. The glass vial stands in the vertical, as confirmed by the horizontal meniscus line of the solvent contained in it.

Figure 17:
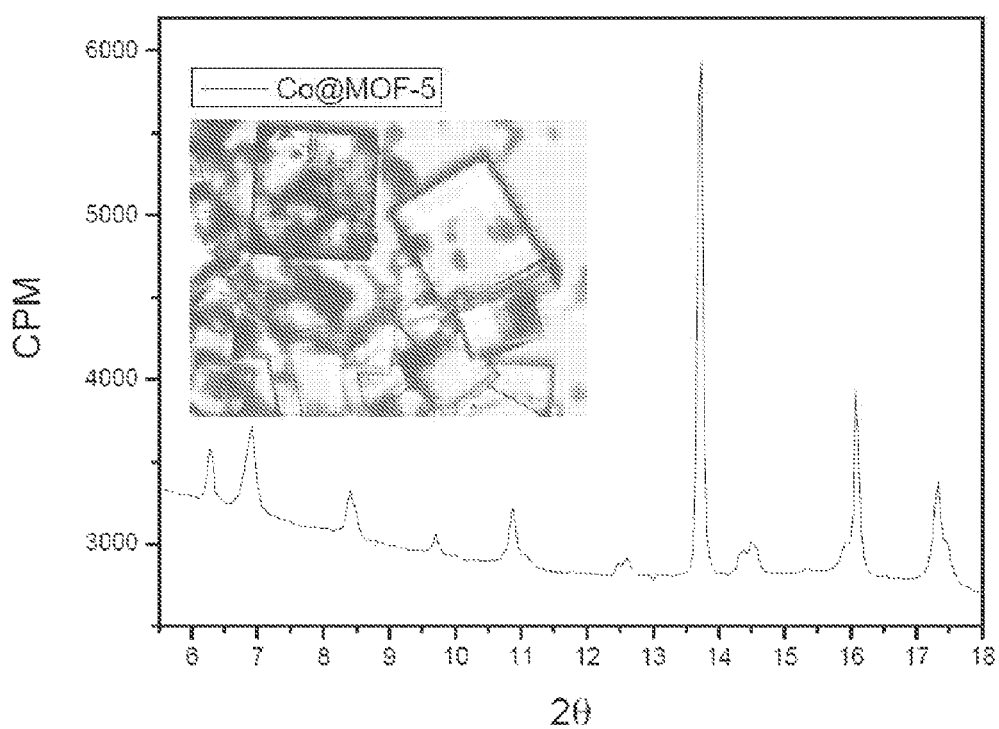
FIG. 17 provides an XRD pattern of MOF-5 crystals containing ferromagnetic Cobalt nanoparticles.

Again, XRD diffraction (FIG. 17) confirmed the formed crystals were MOF-5, with the XRD pattern corresponding to the know XRD pattern for a MOF-5 crystal.

Example 3

Luminescent Crystal Facilitators

Multi core-shell CdSe/CdS/ZnS Quantum Dots (QDs) were used as crystallisation facilitators to nucleate the growth of MOF-5 crystals. The QDs result to be embedded inside MOF-5 crystals after adding a QDs suspension in Dimethylformamide—DMF (or Diethylformamide—DEF) into a typical MOF-5 growing medium, following a similar method as previously described in section 2.1. The following reagents were used:
 $Zn(NO_3)_2$: 0.15 g
 Terephthalic acid: 0.0172 g
 DEF: 4 mL
 QDs suspension in DMF* (or DEF): 0.4 mL (*The concentration of QDs in DMF (or DEF) is 0.2 mM)

Figure 18:
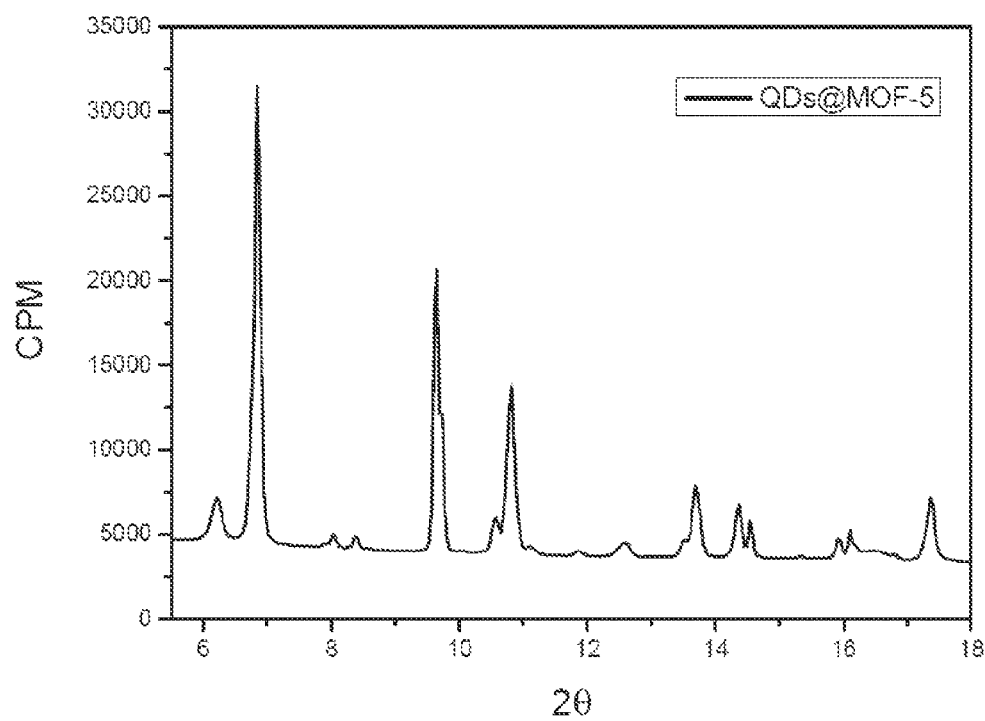
FIG. 18 provides a Photoluminescence emission spectrum of CdSe/CdS/ZnS Quantum Dots crystallisation facilitators according to one embodiment of the present invention embedded inside cubic crystals of MOF-5.

The resulting crystals are cubic in shape and show the typical diffraction pattern of cubic MOF-5 (as best shown in FIG. 18).

Figure 19:
FIG. 19 provides an SEM micrograph showing porous $TiO_2$ beads crystallisation facilitators according to one embodiment of the present invention embedded inside elongated crystals of MOF-5.

The presence of luminescent QDs within the crystals was confirmed using confocal microscopy. Using an excitation laser light at 512 nm, an emission at 640 nm was stimulated. The resulting spatial distribution within the crystal sample is shown in FIG. 19. The image shows the emitted light from a section of one of the QDs@MOF-5 crystals, and confirms presence of QDs inside.

Figure 20:
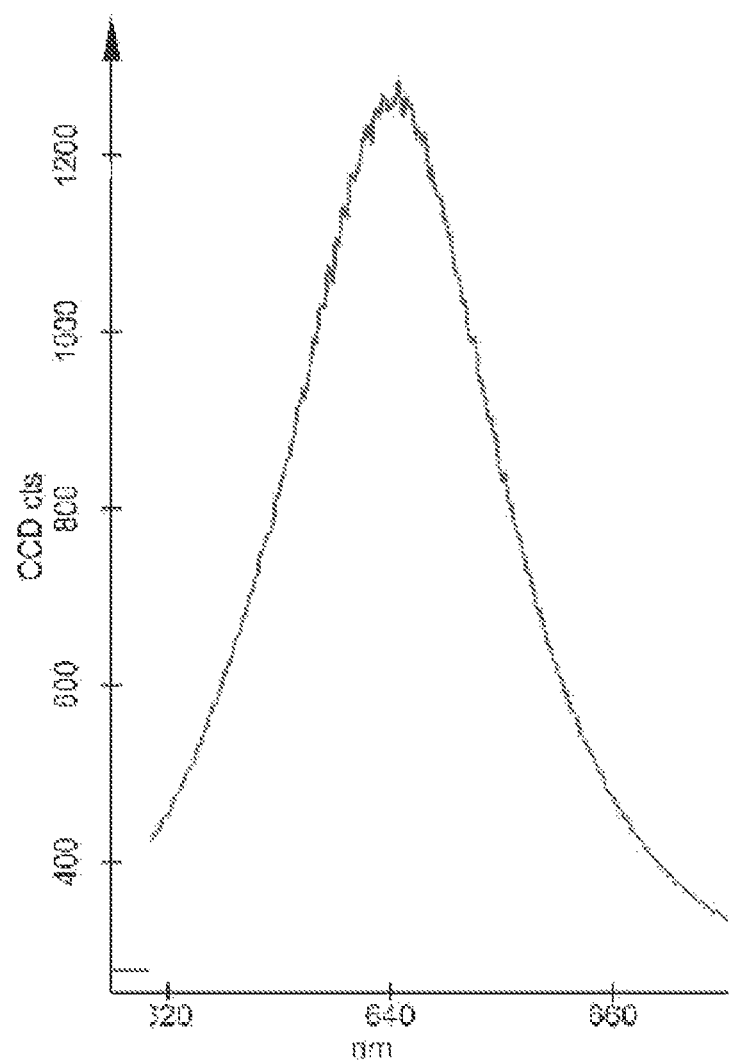
FIG. 20 provides a low angle XRD pattern of elongated crystals nucleated by means of amino-functionalized $TiO_2$ beads crystallisation facilitators.

FIG. 20 shows the emission spectra recorded for QDs embedded inside the MOF-5 crystals. In the specific sample the emission is centred at 640 nm. The spectrum was recorded using a confocal microscope with a 512 nm excitation laser light. The spectra confirm the luminescent properties provided by these crystal facilitators.

The invention described herein is susceptible to variations, modifications and/or additions other than those specifically described and it is to be understood that the invention includes all such variations, modifications and/or additions which fall within the spirit and scope of the above description.

The invention claimed is:

1. A metal-organic framework crystallisation facilitator for promoting crystal growth of a metal-organic framework, the crystallisation facilitator comprising nanoparticles or microparticles of at least one of:
 a compound comprising at least one of Zn, P, Si, B, C, Au or Al or ionic forms thereof combined with at least one of O, S, N or OH or ionic forms thereof; or
 at least one metal, metal chalcogenide or ionic, elemental form thereof,
 wherein the metal organic framework is formed on and around each microparticle or nanoparticle of the crystallisation facilitator.

2. A crystallisation facilitator according to claim 1, wherein the crystallisation facilitator is a substantially spherical shaped particle, nanoparticle and/or microparticle.

3. A crystallisation facilitator according to claim 1, comprising a compound comprising at least one of Zn, P, Si, B, C, Au or Al or ionic forms thereof combined with at least one of O, S, N or OH or ionic forms thereof having a chemical functionality including at least one of vinyl-, mercapto-, carboxyl-, hydroxyl, or other alkyl-groups.

4. A crystallisation facilitator according to claim 1, produced from precursor material including a non-ionic copolymer surfactant.

5. A crystallisation facilitator according to claim 1, comprising at least one metal, metal chalcogenide or ionic, elemental form thereof having at least one of amino-, carboxyl-, or hydroxyl-functionalised surfaces.

6. A crystallisation facilitator according to claim 1, wherein the crystallisation facilitator is a metal or ionic form of that metal is selected from the group consisting of Group 1 through 16 metals of the IUPAC Periodic Table of the Elements including actinides, and lanthanides, and combinations thereof.

7. A crystallisation facilitator according to claim 1, wherein the metal or ionic form of that metal is at least one of ferromagnetic, paramagnetic, superparamagnetic.

8. A crystallisation facilitator according to claim 1, wherein the crystallisation facilitator is a metal chalcogenide comprising a compound, or ionic or elemental form of that compound including a metal M selected from Li, Na, K, Rb, Be, Mg, Ca, Sr, Ba, So, Y, Ti, Zr, Hf, V, Nb, Ta, Cr, Mo, W, Mn, Re, Fe, Ru, Os, Co, Rh, Ir, Ni, Pd, Pt, Cu, Ag, Au, Zn, Cd, Hg, B, Al, Ga, In, Tl, Si, Ge, Sn, Pb, As, Sb, Bi, combined with a element C selected from at least one of O, S, Se, Te.

9. A crystallisation facilitator according to claim 8, in which the metal chalcogenide nanoparticles have a core-shell structure in which the core comprises at least one metal chalcogenide according to claim 8, and the shell comprises at least one metal chalcogenide according to claim 8.

10. A crystallisation facilitator according to claim 1, comprising particles of silicon dioxide with at least one of amino-, carboxyl-, or hydroxyl-functionalised surfaces.

11. A crystallisation facilitator according to claim 1, wherein the particles of the crystallisation facilitator are provided in or on a substrate and are preferably selectively spatially located in or on the substrate.

12. A metal-organic framework containing crystallisation facilitator comprising:
a crystallisation facilitator according to claim 1 captured within the metal organic framework;
a plurality of metal clusters, each metal cluster including one or more metal ions; and
a plurality of charged multidentate linking ligands connecting adjacent metal clusters.

13. A method of synthesising a metal-organic framework including the steps of:
providing a growing medium including precursors for forming a metal-organic framework comprising a plurality of metal clusters, each metal cluster including one or more metal ions; and a plurality of charged multidentate linking ligands connecting adjacent metal clusters;
introducing a crystallisation facilitator according to claim 1 or reagents which form a crystallisation facilitator according to claim 1 insitu into the growing medium; and
inducing the formation of the metal-organic framework on the crystallisation facilitator surface,
wherein the metal organic framework is formed on and around each microparticle or nanoparticle of the crystallisation facilitator.

14. A method of synthesising a metal-organic framework according to claim 13, wherein each metal cluster comprises two or more metal ions and each ligand of the plurality of multidentate ligand includes two or more carboxylates.

15. A method of synthesising a metal-organic framework according to claim 13, wherein the metal ion of the metal cluster is selected from the group consisting of Group 1 through 16 metals of the IUPAC Periodic Table of the Elements including actinides, and lanthanides, and combinations thereof.

16. A method of synthesising a metal-organic framework according to claim 13, wherein the metal cluster has formula $M_mX_n$ where M is a metal ion, X is selected from the group consisting of Group 14 through Group 17 anions, m is an number from 1 to 10, and n is a number selected to charge balance the metal cluster so that the metal cluster has a predetermined electric charge and wherein X is selected from the group consisting of $O^{2-}$, $N^{3-}$, and $S^{2-}$.

17. A method of synthesising a metal-organic framework according to claim 13, wherein the multidentate linking ligand has 6 or more atoms that are incorporated in aromatic rings or non-aromatic rings.

18. A method of synthesising a metal-organic framework according to claim 13, wherein the crystallisation facilitator is formed within the growing medium from precursor compounds introduced into the growing medium.

19. A method of synthesising a metal-organic framework according to claim 13, further comprising introducing a functional species into the growing medium, the functional species being encapsulated within the nanoparticles of the crystallisation facilitator within the metal organic framework.

20. A metal organic framework containing crystallisation facilitator captured within the metal organic framework, formed from a method according to claim 13.

* * * * *